United States Patent
Shalon et al.

(10) Patent No.: US 7,914,468 B2
(45) Date of Patent: Mar. 29, 2011

(54) SYSTEMS AND METHODS FOR MONITORING AND MODIFYING BEHAVIOR

(75) Inventors: Tadmor Shalon, Palo Alto, CA (US); Tidhar Shalon, Tel-Aviv (IL)

(73) Assignee: SVIP 4 LLC, Palo Alto, CA (US)

( * ) Notice: Subject to any disclaimer, the term of this patent is extended or adjusted under 35 U.S.C. 154(b) by 1011 days.

(21) Appl. No.: 11/230,645

(22) Filed: Sep. 21, 2005

(65) Prior Publication Data
US 2006/0064037 A1 Mar. 23, 2006

Related U.S. Application Data

(60) Provisional application No. 60/612,292, filed on Sep. 22, 2004.

(51) Int. Cl.
*A61B 5/103* (2006.01)
*A61B 5/117* (2006.01)

(52) U.S. Cl. ........ 600/590; 600/587; 600/589; 600/593; 600/595

(58) Field of Classification Search .................. 600/586, 600/587, 590, 593, 595, 589
See application file for complete search history.

(56) References Cited

U.S. PATENT DOCUMENTS

| | | | |
|---|---|---|---|
| 2,674,808 A | 4/1954 | Tainter | |
| 4,823,808 A | 4/1989 | Clegg et al. | |
| 4,836,778 A | 6/1989 | Baumrind et al. | |
| 5,067,488 A | 11/1991 | Fukada et al. | |
| 5,188,104 A | 2/1993 | Warnicke et al. | |
| 5,263,480 A | 11/1993 | Warnicke et al. | |
| 5,263,491 A | 11/1993 | Thornton | |
| 5,301,679 A | 4/1994 | Taylor | |
| 5,398,688 A | 3/1995 | Laniado | |
| 5,447,489 A | 9/1995 | Issalene et al. | |
| H1497 H | 10/1995 | Marshall | |
| 5,673,691 A | 10/1997 | Abrams et al. | |
| 5,757,929 A | 5/1998 | Wang et al. | |
| 5,901,660 A | 5/1999 | Stein | |
| 6,135,950 A | 10/2000 | Adams | |
| 6,605,038 B1 | 8/2003 | Teller et al. | |
| 6,735,477 B2 | 5/2004 | Levine | |
| 6,735,563 B1 | 5/2004 | Bi | |

(Continued)

FOREIGN PATENT DOCUMENTS
EP 0338593 10/1989
(Continued)

OTHER PUBLICATIONS

Perlman et al. "Effects of Age, Gender, Bolus Volume, and Bolus Viscosity on Oropharyngeal Pressure During Swallowing", Journal of Applied Physiology, 75(1): 33-37, 1993. Abstract.

(Continued)

*Primary Examiner* — Max Hindenburg
*Assistant Examiner* — Adam J Eiseman
(74) *Attorney, Agent, or Firm* — Shay Glenn LLP

(57) ABSTRACT

A system for detecting non-verbal acoustic energy generated by a subject is provided. The system includes a sensor mountable on or in a body region of the subject, the sensor being capable of sensing the non-verbal acoustic energy; and a processing unit being capable of processing the non-verbal acoustic energy sensed by the sensor and deriving an activity related signature therefrom, thereby enabling identification of a specific activity associated with the non-verbal acoustic energy.

22 Claims, 12 Drawing Sheets
(10 of 12 Drawing Sheet(s) Filed in Color)

Caloric control mode data flow diagram

U.S. PATENT DOCUMENTS

| | | | |
|---|---|---|---|
| 7,433,484 | B2 | 10/2008 | Asseily et al. |
| 2001/0049470 | A1 | 12/2001 | Mault et al. |
| 2002/0077831 | A1 | 6/2002 | Numa |
| 2002/0138115 | A1 | 9/2002 | Baumann et al. |
| 2002/0156398 | A1* | 10/2002 | Mansy et al. ............. 600/586 |
| 2003/0009202 | A1 | 1/2003 | Levine |
| 2003/0055654 | A1 | 3/2003 | Oudeyer |
| 2003/0147544 | A1 | 8/2003 | Lichtblau |
| 2003/0152607 | A1 | 8/2003 | Mault |
| 2004/0034289 | A1 | 2/2004 | Teller et al. |
| 2004/0059393 | A1 | 3/2004 | Policker et al. |
| 2004/0073142 | A1 | 4/2004 | Takeuchi et al. |
| 2004/0133081 | A1 | 7/2004 | Teller et al. |
| 2004/0147816 | A1 | 7/2004 | Policker et al. |
| 2004/0152957 | A1 | 8/2004 | Stivoric et al. |
| 2005/0096514 | A1* | 5/2005 | Starkebaum ............. 600/309 |
| 2005/0096637 | A1 | 5/2005 | Heruth |
| 2005/0283096 | A1* | 12/2005 | Chau et al. ............. 600/593 |

FOREIGN PATENT DOCUMENTS

| | | |
|---|---|---|
| FR | 2800266 | 4/2001 |
| JP | 7213510 | 8/1995 |
| JP | 09054819 | 2/1997 |
| JP | 10011560 | 1/1998 |
| JP | 10016809 | 1/1998 |
| JP | 11318862 | 1/1999 |
| JP | 11206740 | 3/1999 |
| JP | 11123185 | 5/1999 |
| JP | 10377740 | 6/2000 |
| JP | 200166899 | 6/2000 |
| JP | 2001308206 | 2/2001 |
| JP | 2225320 | 9/2002 |
| JP | 2002253520 | 9/2002 |
| JP | 2003111748 | 4/2003 |
| JP | 23250198 | 5/2003 |
| JP | 24057585 | 2/2004 |
| JP | 2004057585 | 2/2004 |
| WO | WO 02/26101 | 4/2002 |
| WO | WO 02/053093 | 7/2002 |
| WO | WO 03/032629 | 4/2003 |
| WO | WO 03/032681 | 4/2003 |

OTHER PUBLICATIONS

Perlman et al. "Respiratory and Acoustic Signals Associated With Bolus Passage During Swallowing", Dysphagia, 15(2): 89-94, 2000. Abstract.

Gupta et al. "Surface EMG Measurements at the Throat During Dry and Wet Swallowing", Dysphagia, 11(3): 173-179, 1996. Abstract.

Mack et al. "Non-Invasive Analysis of Physiological Signals (NAPS): A Vibration Sensor That Passively Detects Heart and Respiration Rates as Part of a Sensor Suite for Medical Monitoring", Summer Bioengineering Conference, Key Biscayne, Fa., p. 1071-1072, 2003.

Preiksaitis et al. "Coordination of Respiration and Swallowing: Effect of Bolus Volume in Normal Adults", American Journal of Physiology, 263(Regulatory Integrative Comp. Physiol.32): R624-R630, 1992.

Chia et al. "Portable Patient Training Device for Lung Cancer Treatment", Final Report, University of Wisconsin-Madison, College of Engineering, Biomedical Engineering 301, p. 1-32, 2004.

Brown "Elasticated Chest/Abdomen Strap With Piezo Film Sensor", Measurement Specialities, Sensor Products Division (Europe), RB 09/00: 3 P., 2000.

McCool et al. "Tidal Volume and Respiratory Timing Derived From A Portable Ventilation Monitor", Clinical Investigations in Critical Care (Chest), 122: 684-691, 2002.

Preiksaitis et al. "Coordination of Breathing and Swallowing: Effects of Bolus Consistency and Presentation in Normal Adults", Journal of Applied Physiology, 81(4): 1707-1714, 1996.

Tarrant et al. "Comparative Reviews of Techniques for Recording Respiratory Events at Rest and During Deglutition", Dysphagia, 12: 24-38, 1997.

Yeomans "Rating Changes Over the Course of Meals: What Do They Tell Us About Motivation to Eat?" Neuroscience and Biobehavioral Reviews, 24: 249-259, 2000.

Stellar et al. "Chews and Swallows and the Microstructure of Eating", The American Journal of Clinical Nutrition, 42: 973-982, 1985.

Spiegel "Rate of Intake, Bites, and Chews—The Interpretation of Lean-Obese Differences", Neuroscience and Biobehavioral Reviews, 24: 229-237, 2000.

Bellisle et al. "Chewing and Swallowing as Indices of the Stimulation to Eat During Meals in Humans: Effects Revealed by the Edogram Method and Video Recordings", Neuroscience and Biobehavioral Reviews, 24: 223-228, 2000.

??? "Product Catalog", Ambulatory Monitoring, www.ambulatory-monitory.com, 7 P.

Cichero et al. "Acoustic Signature of the Normal Swallow: Characterization by Age, Gender, and Bolus Volume", Ann. Otol. Rhino. Laryngol., 111(7 pt 1): 623-632, 2002. Abstract.

Takahashi et al. "Methodology for Detecting Swallowing Sounds", Dysphagia, 9(1): 54-62, 1994. Abstract.

Takahashi et al. "Symmetry and Reproducibility of Swallowing Sounds", Dysphagia, 9(3): 168-173, 1994. Abstract.

Cichero et al. "Detection of Swallowing Sounds: Methodology Revisited", Dysphagia, 17(1): 40-49, 2002. Abstract.

International Preliminary Report on Patentability Dated Apr. 5, 2007 From the International Bureau of WIPO Re.: Application No. PCT/IL2005/001008.

International Search Report Dated Jan. 12, 2006 From the International Searching Authority Re.: Application No. PCT/IL2005/001008.

Written Opinion Dated Jan. 12, 2006 From the International Searching Authority Re.: Application No. PCT/IL2005/001008.

IPRP CH I.

Oliveira; The Active Ear Canal; J Am Acad Audiol; vol. 8; No. 6; pp. 401-410; Dec. 1997.

* cited by examiner

Figs. 1a-d

SYSTEMS AND METHODS FOR MONITORING AND MODIFYING BEHAVIOR

RELATED APPLICATIONS

The present application claims priority from U.S. Provisional Patent Application No. 60/612,292, filed on Sep. 22, 2004. The content of the above Application is incorporated herein by reference.

FIELD AND BACKGROUND OF THE INVENTION

The present invention relates to systems and methods for monitoring and modifying behavior of a subject such as a human or an animal.

Successful dieting requires long-term behavior modification in terms of eating and physical activity. A diet plan is only part of the solution. Sticking to the plan requires behavior modification that is generally beyond the ability of most people to implement without external assistance. There does not appear to be a diet or process by which people can reliably lose weight and keep it off. Numerous studies have shown 100% weight regain on most diets. Other meta-studies show that people regain approximately 75% of the initial weight loss after five years.

Assessing energy balance, i.e. the net difference between energy intake and expenditure is central to obesity research, prevention, and treatment. The importance of accurately measuring energy balance is appreciated by considering the dynamics of average weight gain in middle aged adults which is about 10 lbs. per decade. This significant gain in weight follows from a net intake excess of approximately 0.3% of the daily calorie consumption, which is below the awareness of most individuals. [National Institutes of Health, Bioengineering Approaches To Energy Balance And Obesity (SBIR/STTR). http://grants1.nih.gov/grants/guide/pa-files/PA-04-156.html].

Today, energy intake is at best only crudely measured by self reporting food consumed, an approach that nutritionists know falls well short of its accuracy goals. Although standard self-report questionnaire and recall techniques can provide valuable data on dietary patterns, these techniques are time consuming, inconvenient, and infamous for considerable underreporting of food consumed, with this error more pronounced for over weight than non-over weight individuals.

Several devices and methods which attempt to overcome the deficiencies of self reporting approaches have been described in the prior art.

U.S. Pat. No. 6,135,950 describes a pager size device to aid in controlling a person's daily food intake. U.S. Pat. No. 5,398,688 describes a timer for calculating and alerting a user when their maximum eating time has expired. U.S. Pat. Nos. 5,188,104 and 5,263,480 describe the treatment of eating disorders by nerve stimulation by detecting preselected events indicative of imminent need for treatment and applying predetermined stimulating signal to patient vagus nerve. PCT Publication WO 02/053093 and U.S. application Publication No. 2004/0147816, describe a similar invasive technique except that the stimulation is driven into the stomach muscle of the subject, thereby altering the timing of digestion. PCT Publication No. WO 02/026101, describes a generic arrangement of implantable sensors, microprocessors and a negative-feedback stimulator which can enforce a corrective regimen on a patient suffering from a dietary or other behavioral disorder.

Unfortunately none of the approaches described above have been shown to be effective. The only non-drug interventions for losing weight that display some long-term efficacy are the various procedures to reduce the volume of the stomach or bypass it altogether so that just a small volume of food may satiate the patient. While such approaches show some promise, they require invasive surgical procedures with attendant risks and pain, they often require permanent prosthetic implants and/or irreversible modification of the patient's digestive tract with potentially serious complications and side effects, they are costly, and they require long recovery time during which the patient is immobile and unproductive. Many of those who are overweight or obese are thus unable or unwilling to undergo such interventions.

There is thus a widely recognized need for, and it would be highly advantageous to have, a system and method for controlling eating behavior without the invasiveness, risks, pain, complications, cost, and recovery time associated with stomach volume reduction and bypass procedures.

SUMMARY OF THE INVENTION

According to one aspect of the present invention there is provided a system for detecting activity related to non-verbal acoustic energy generated by a subject comprising: (a) a sensor mountable on or in a body region of the subject, the sensor being capable of sensing the non-verbal acoustic energy; and (b) a processing unit being capable of processing the non-verbal acoustic energy sensed by the sensor and deriving an activity related signature therefrom, thereby enabling classification of a specific activity associated with the non-verbal acoustic energy.

According to further features in preferred embodiments of the invention described below, the sensor is a microphone.

According to still further features in the described preferred embodiments the sensor is a bone conduction microphone.

According to still further features in the described preferred embodiments the sensor is mountable on a head of the subject.

According to still further features in the described preferred embodiments the sensor is mountable behind the ear.

According to still further features in the described preferred embodiments the sensor is implantable.

According to still further features in the described preferred embodiments the sensor and the processing unit are housed in a single device.

According to still further features in the described preferred embodiments the sensor and the processing are separately housed.

According to still further features in the described preferred embodiments the system further comprises at least one addition sensor selected from the group consisting of a heart rate sensor, an accelerometer, a skin conductance sensor, a muscle tone sensor, a blood sugar level sense, a bite sensor and a stomach contraction sensor.

According to still further features in the described preferred embodiments the system further comprises at least one feedback device.

According to still further features in the described preferred embodiments the at least one feedback device is a speaker.

According to still further features in the described preferred embodiments the at least one feedback device is selected from the group consisting of lights, a graphical display, an electrical stimulation device, a buzzer, a vibrating element and a chemical dispensing unit.

According to still further features in the described preferred embodiments the processing unit forms a part of a device selected from the group consisting of a PDA, a cell phone, a wristwatch, a portable media player and a computer.

According to still further features in the described preferred embodiments the sensor is mountable within an ear canal of the subject.

According to still further features in the described preferred embodiments the sensor is mountable within the oral cavity of the subject.

According to still further features in the described preferred embodiments the at least one feedback device and the at least one sensor are housed within a single device.

According to still further features in the described preferred embodiments the at least one feedback device and the at least one sensor are a single device.

According to still further features in the described preferred embodiments the sensor and the processing unit are connected through a wired connection.

According to still further features in the described preferred embodiments the sensor and the processing unit are connected through a wireless connection.

According to still further features in the described preferred embodiments the wireless connection is effected through radiofrequency or infrared.

According to another aspect of the present invention there is provided a system for monitoring ingestion activity of a subject comprising: (a) a sensor mountable on or in a body region of the subject, the sensor being capable of sensing ingestion related motion or acoustic energy; and (b) a processing unit being capable of processing the ingestion related motion or acoustic energy and deriving an ingestion activity related signature therefrom, thereby monitoring ingestion activity of the subject.

According to still further features in the described preferred embodiments the ingestion related motion or the acoustic energy is generated by jaw motion.

According to still further features in the described preferred embodiments the ingestion related motion or the acoustic energy is generated by stomach contractions or bowel motility.

According to still further features in the described preferred embodiments the ingestion related motion or acoustic energy is generated by biting, chewing or swallowing.

According to still further features in the described preferred embodiments the acoustic energy is non-verbal acoustic activity.

According to still further features in the described preferred embodiments the sensor is mountable within the oral cavity of the subject.

According to still further features in the described preferred embodiments the ingestion activity related signature identifies a type and/or quantity of food or drink consumed.

According to yet another aspect of the present invention there is provided a method of detecting activity related to non-verbal acoustic energy generated by a subject comprising: (a) sensing the non-verbal acoustic energy; and (b) processing the non-verbal acoustic energy and deriving an activity related signature therefrom, thereby enabling classification of a specific activity associated with the non-verbal acoustic energy.

According to still further features in the described preferred embodiments (a) and (b) are conducted over a time period such that a plurality of activity related signatures are obtained.

According to still further features in the described preferred embodiments the method further comprises (c) processing the plurality of activity related signatures to thereby infer a behavior of the subject.

According to still further features in the described preferred embodiments the method further comprises (d) providing feedback to the subject intended to modify the behavior of the subject.

According to still further features in the described preferred embodiments the activity related to non-verbal acoustic energy is eating or drinking.

According to still further features in the described preferred embodiments the specific activity is breathing.

According to still another aspect of the present invention there is provided a method of monitoring ingestion activity of a subject comprising: (a) sensing ingestion related motion or acoustic energy; and (b) processing the ingestion related motion or acoustic energy and deriving an ingestion activity related signature therefrom, thereby monitoring ingestion activity of the subject.

According to still further features in the described preferred embodiments (a) and (b) are conducted over a time period such that a plurality of ingestion activity related signatures are obtained.

According to still further features in the described preferred embodiments the method further comprises (c) processing the plurality of ingestion activity related signatures to thereby determine a ingestion behavior of the subject.

According to still further features in the described preferred embodiments the ingestion activity related signature identifies consumption of a specific food item.

According to an additional aspect of the present invention there is provided a method of accumulating data relating to ingestion behavior of a subject comprising (a) monitoring ingestion related activity of the subject over a time period; (b) generating a signature classifying the ingestion related activity of the subject over the time period; (c) computationally logging the signature thereby accumulating data relating to ingestion behavior of the subject.

According to still further features in the described preferred embodiments the method further comprising associating the signature with a duration of ingestion, rate of ingestion, food mass, volume, caloric value or nutritional value of material ingested prior to, or following step (c).

According to still further features in the described preferred embodiments the method further comprises aggregating the data relating to ingestion behavior for a plurality of subjects into a database.

According to still further features in the described preferred embodiments the method further comprises repeating steps (a)-(c) thereby accumulating data comprising a plurality of distinct signatures.

According to still further features in the described preferred embodiments (a) is effected by counting a number of bites chews and/or swallows over the time period.

According to still further features in the described preferred embodiments the signature reflects the number of bites chews and/or swallows over the time period.

According to still further features in the described preferred embodiments the signature further reflects a sequence of the bites chews and/or swallows over the time period.

According to still further features in the described preferred embodiments the counting is effected by user mounted device.

According to still further features in the described preferred embodiments the device is capable of sensing ingestion activity related motion or acoustic energy.

According to an additional aspect of the present invention there is provided a computer readable medium comprising a database stored therein the database including a plurality of signatures each classifying an ingestion related activity of a subject over a time period.

According to still further features in the described preferred embodiments the database contains ingestion related activity collected from a plurality of subjects.

According to still further features in the described preferred embodiments the signature reflects a number of bites chews and/or swallows over the time period.

According to still further features in the described preferred embodiments the signature further reflects a sequence of the bites chews and/or swallows over the time period According to an additional aspect of the present invention there is provided a device for monitoring food and/or drink consumption of a subject comprising (a) a sensor for sensing ingestion activity of the subject; and (b) at least one feedback device for providing feedback relating to the ingestion activity to the subject.

According to still further features in the described preferred embodiments the device further comprises a processing unit for processing ingestion activity sensed by the sensor.

According to still further features in the described preferred embodiments the device further comprises a data input unit capable of being programmed with the weight, body mass index or fat content of the subject.

According to still further features in the described preferred embodiments the device further comprises a memory unit storing a database including ingestion activity of the subject.

According to still further features in the described preferred embodiments the feedback provided by the feedback device is determined by the device according to the database.

According to still further features in the described preferred embodiments the device further comprises a memory unit storing a database including desired ingestion behavior of the subject.

According to still further features in the described preferred embodiments the feedback provided by the feedback device is determined by the device according to the desired ingestion behavior of the subject.

According to still further features in the described preferred embodiments the at least one feedback device is capable of providing audio feedback.

According to still further features in the described preferred embodiments the device further comprising a data transfer unit for transmitting data pertaining to the ingestion activity of the subject.

According to still further features in the described preferred embodiments the data transfer unit forms a part of a transceiver.

According to still further features in the described preferred embodiments the device further comprises a microphone for receiving acoustic input from the subject.

According to still further features in the described preferred embodiments the device further comprises a processing unit for processing the acoustic input from the subject into data relatable to the ingestion activity sensed by the device.

According to an additional aspect of the present invention there is provided a device for monitoring food and/or drink consumption of a subject comprising (a) a sensor for sensing ingestion activity of the subject; and (b) a data transfer unit for transmitting data relating to the ingestion activity of the subject.

The present invention successfully addresses the shortcomings of the presently known configurations by providing a system and method of detecting activity patterns and feeding back information about these activity patterns to the user in real time.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1:
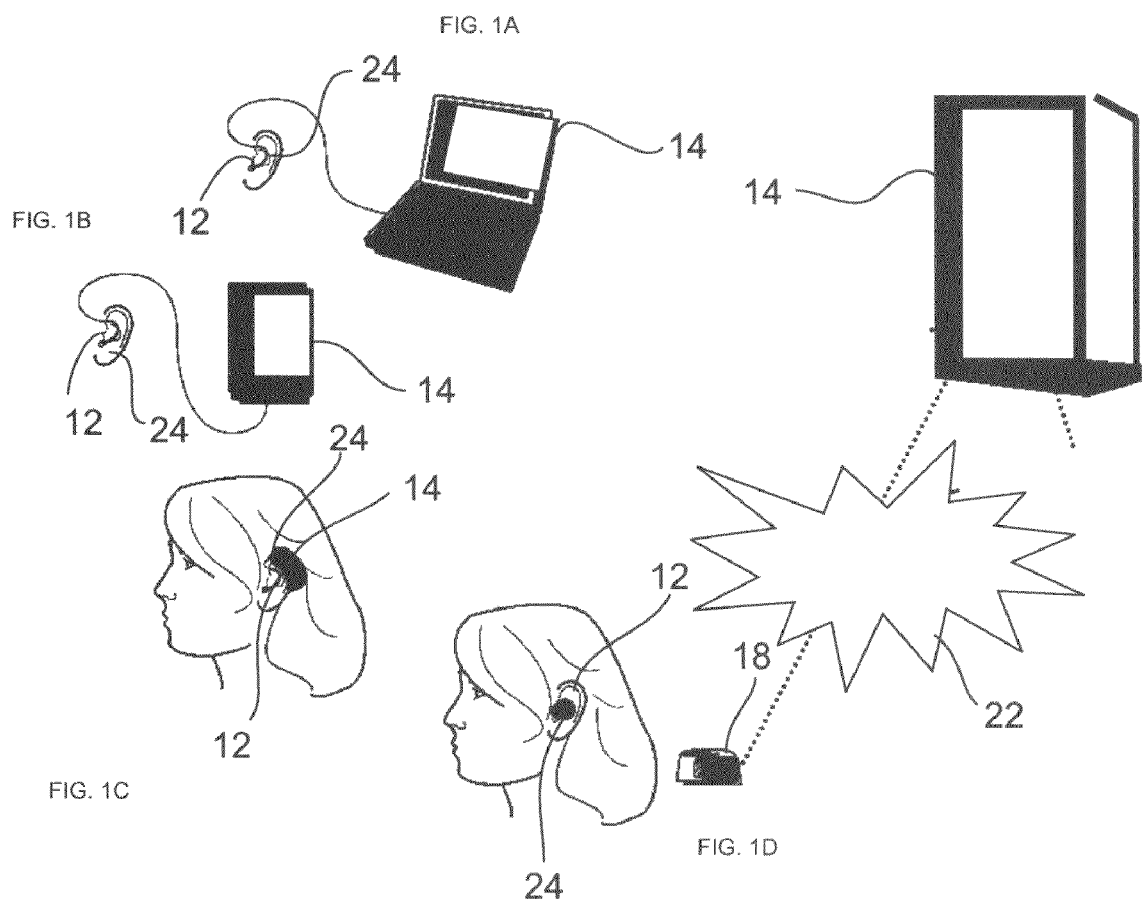
Figure 2:
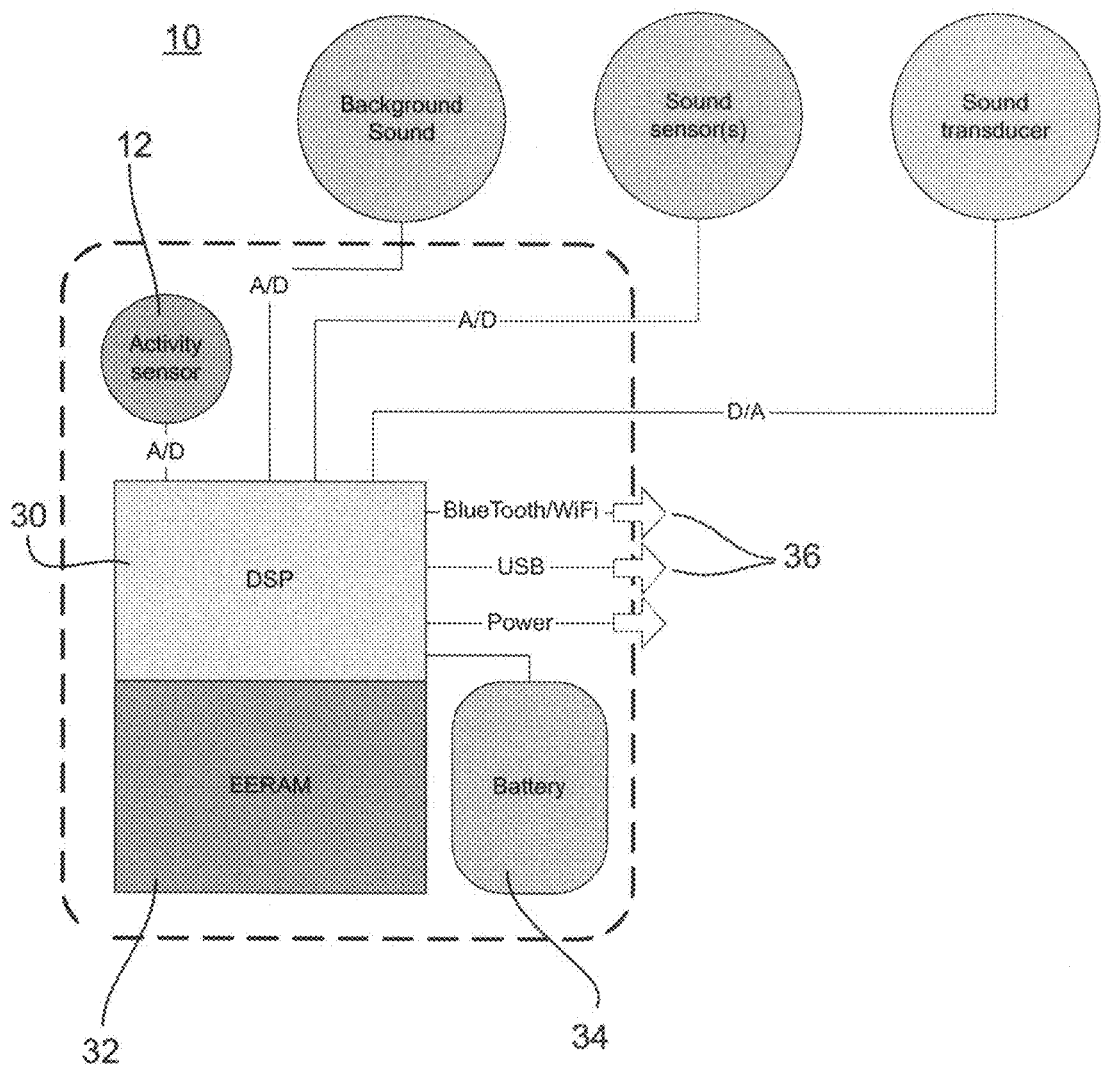
Figure 3:
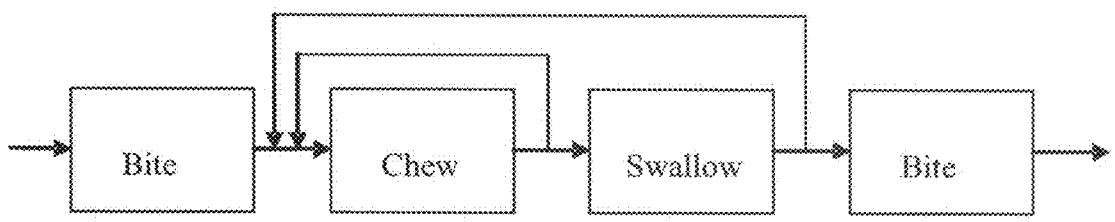
Figure 4:
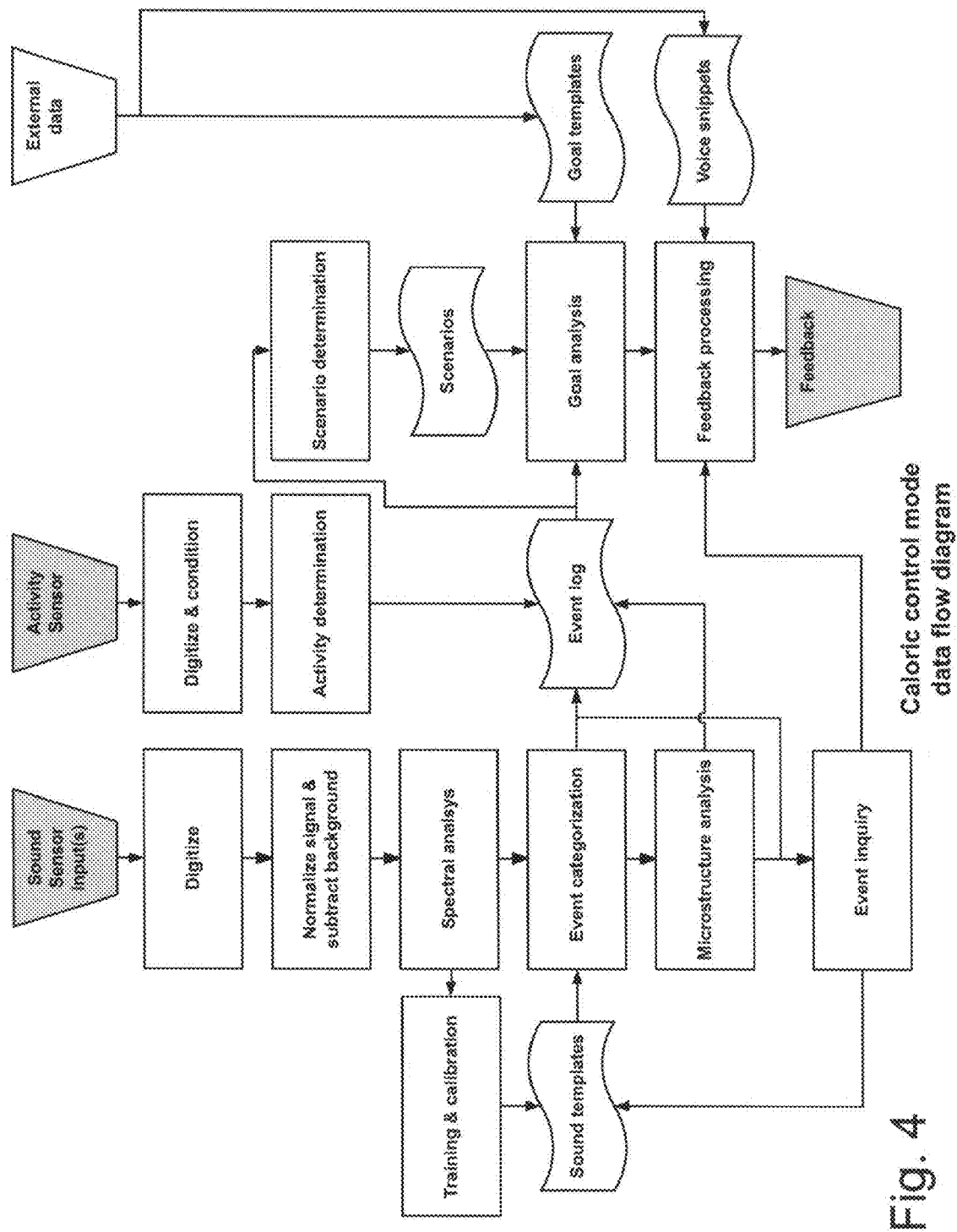
Figure 5:
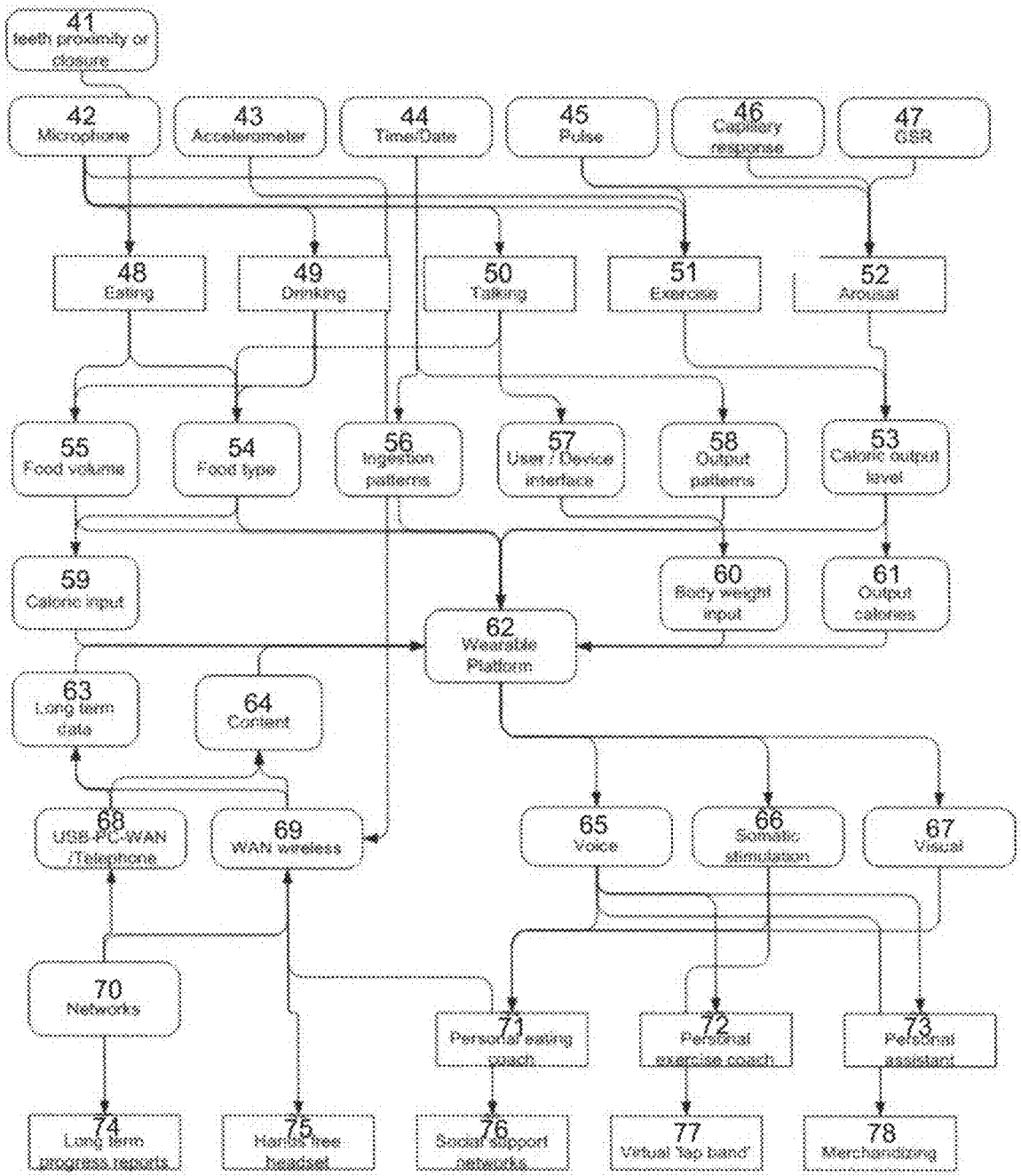
Figure 6:
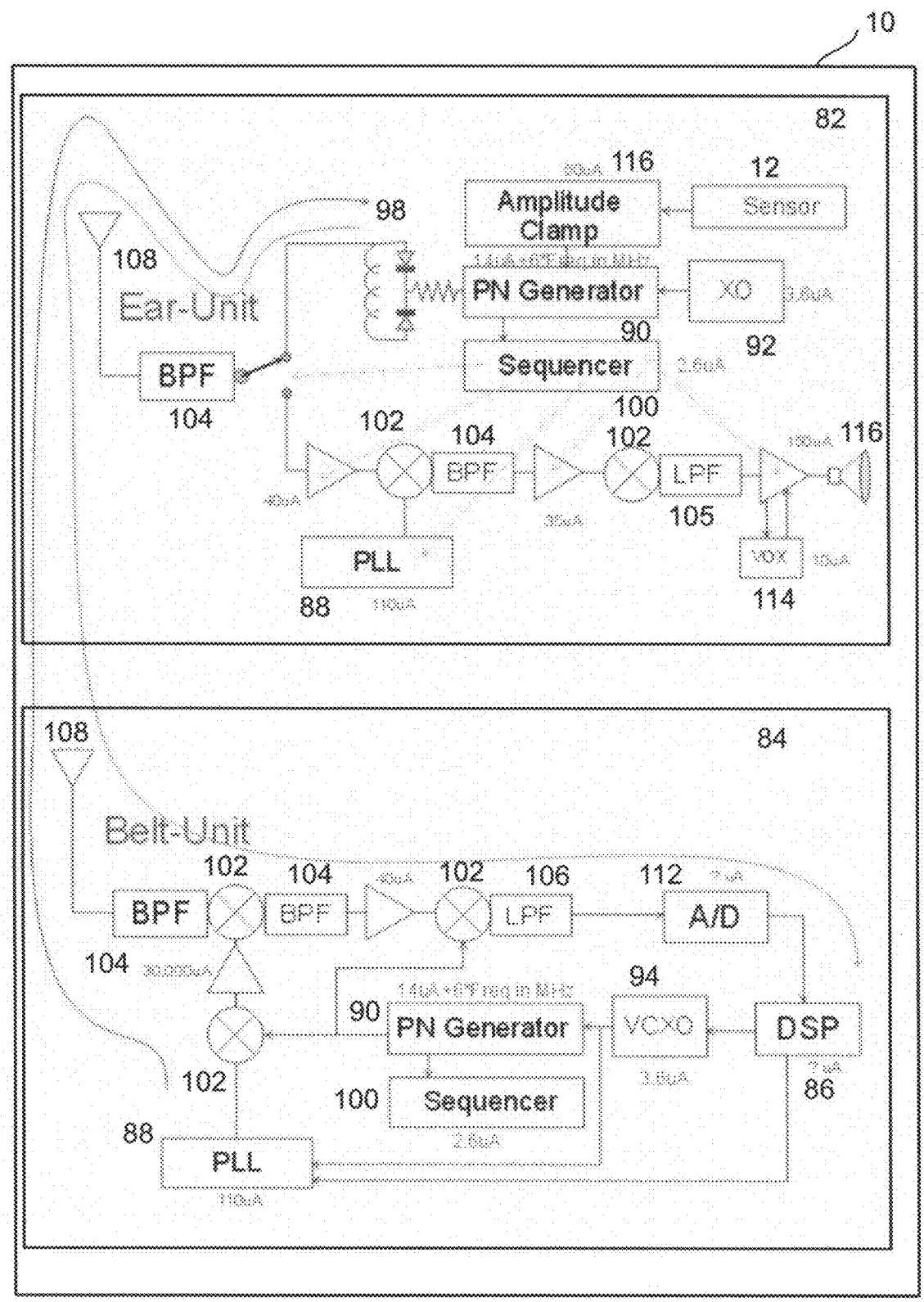
Figure 7:
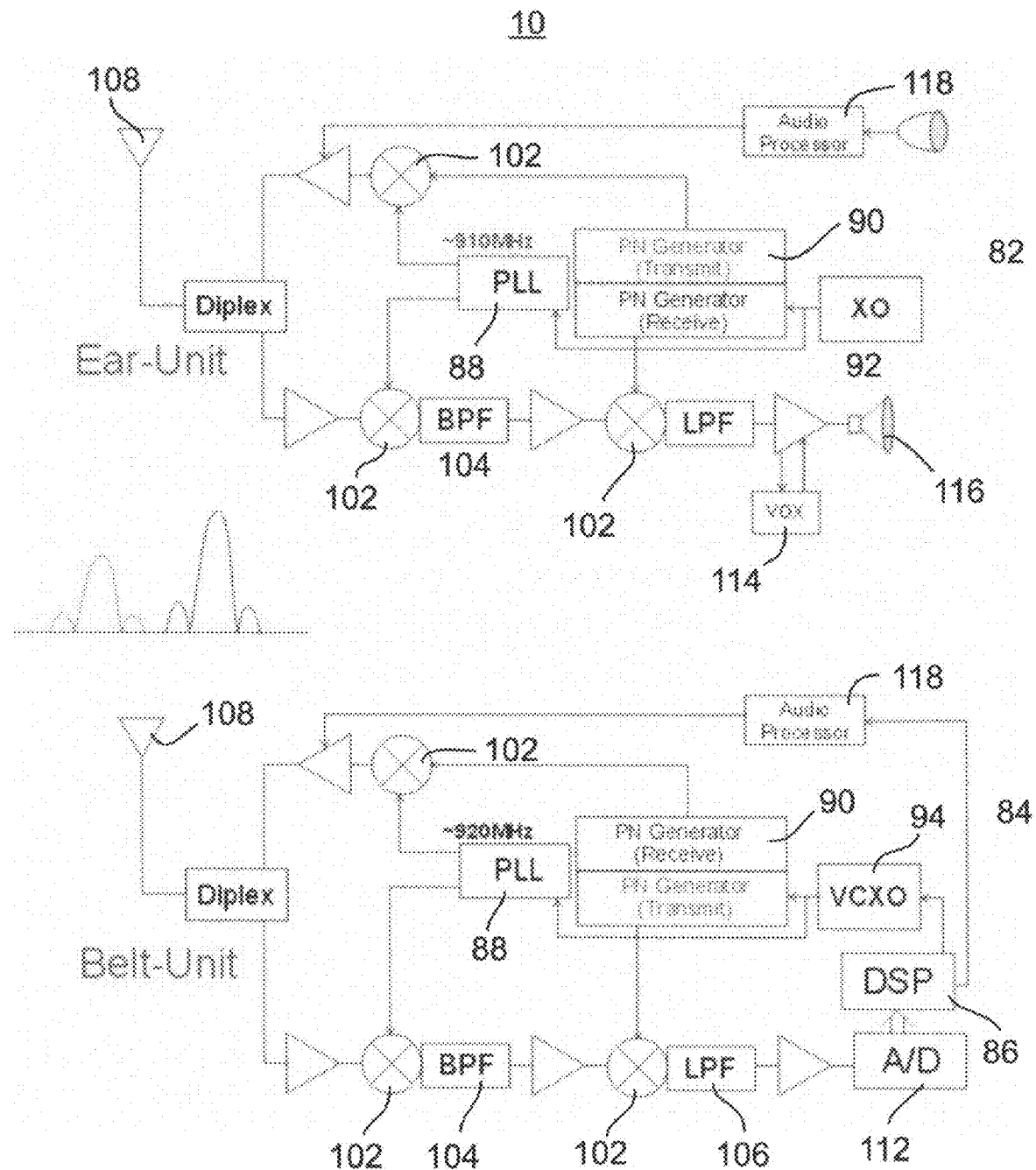
Figure 8:
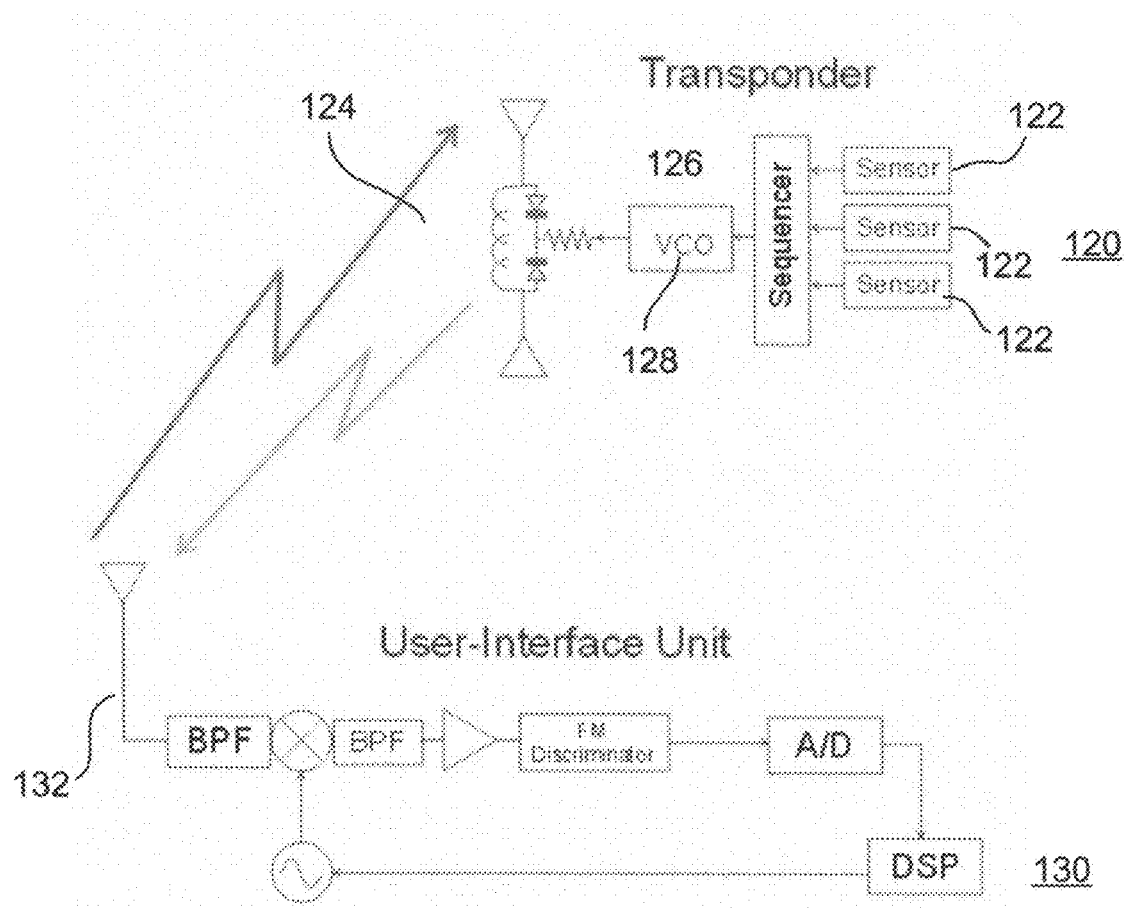
Figure 9:
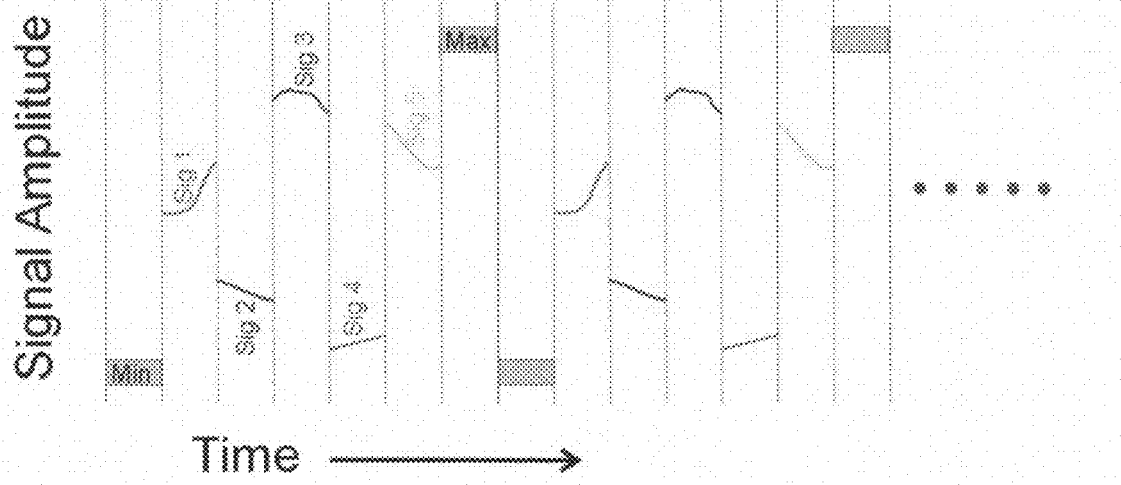
Figure 10:
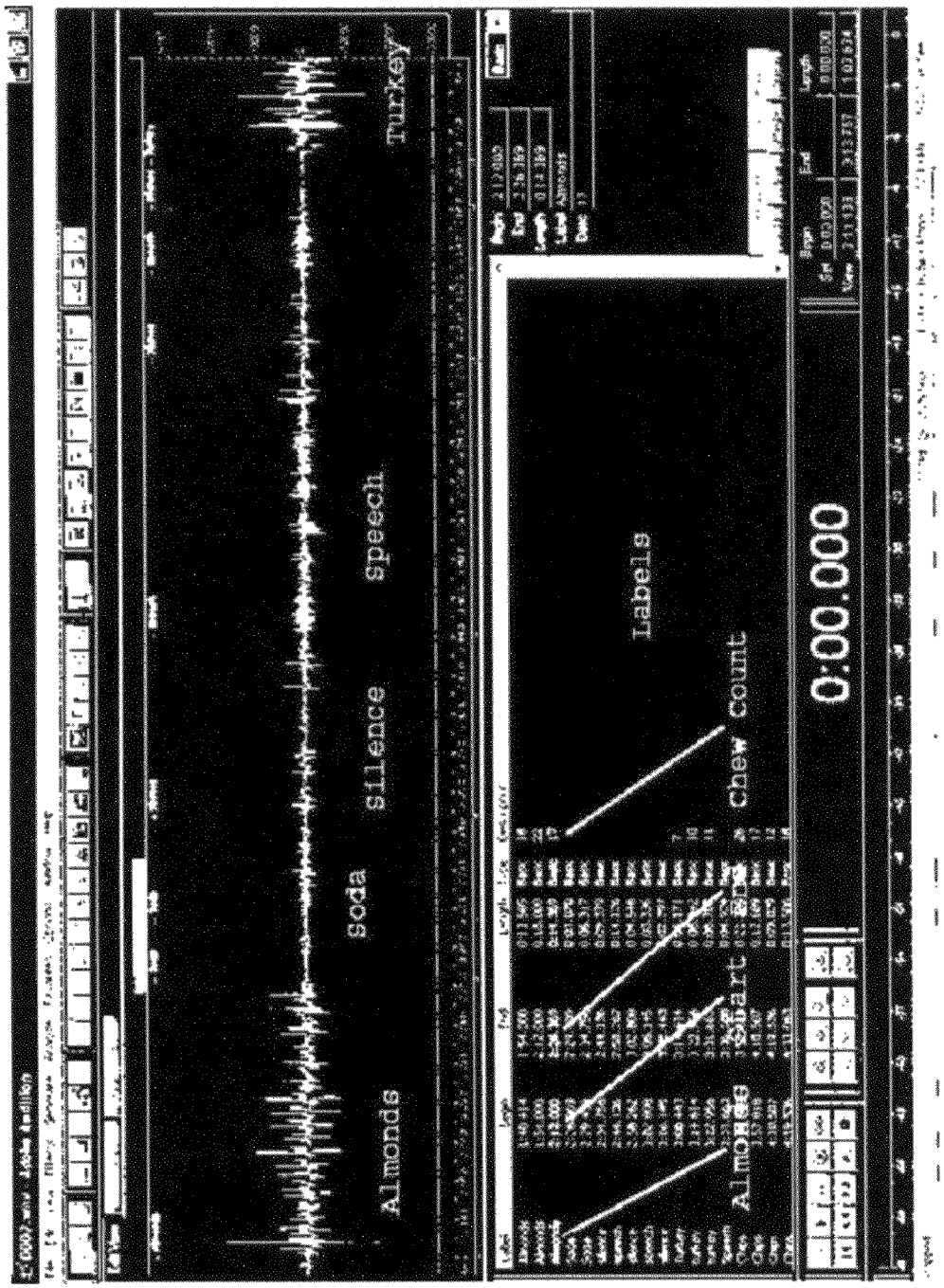
Figure 11:
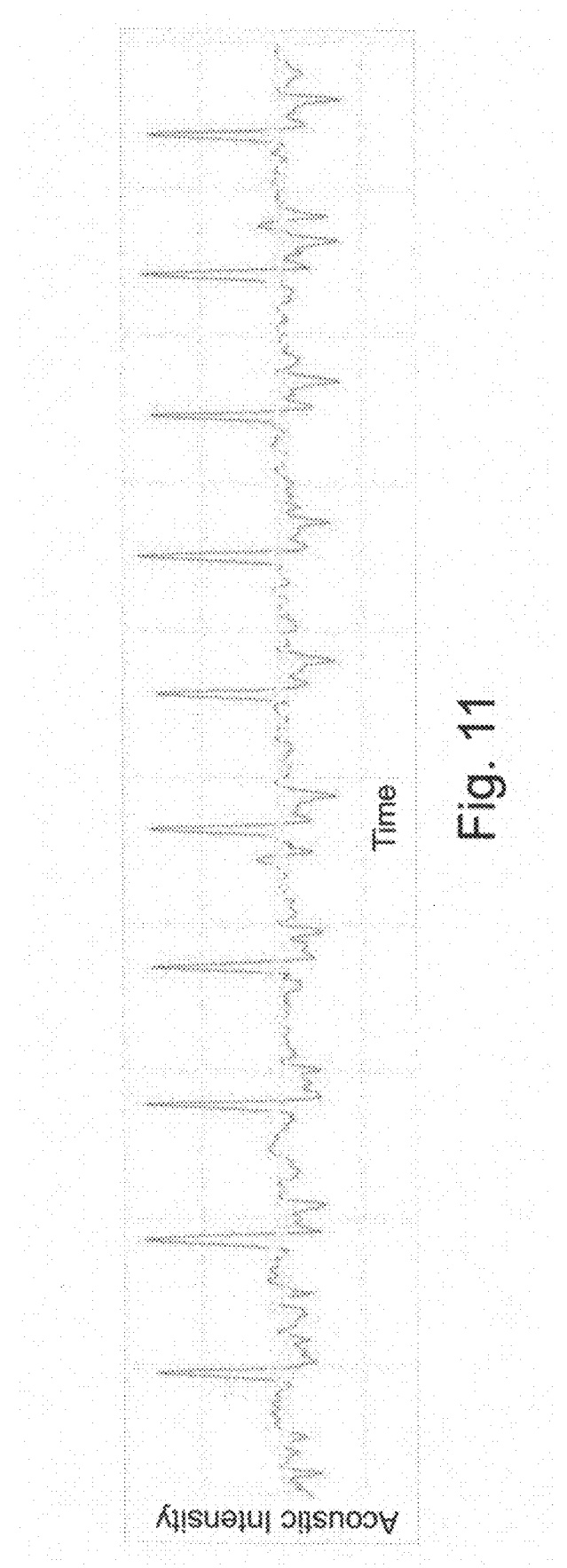
Figure 12:
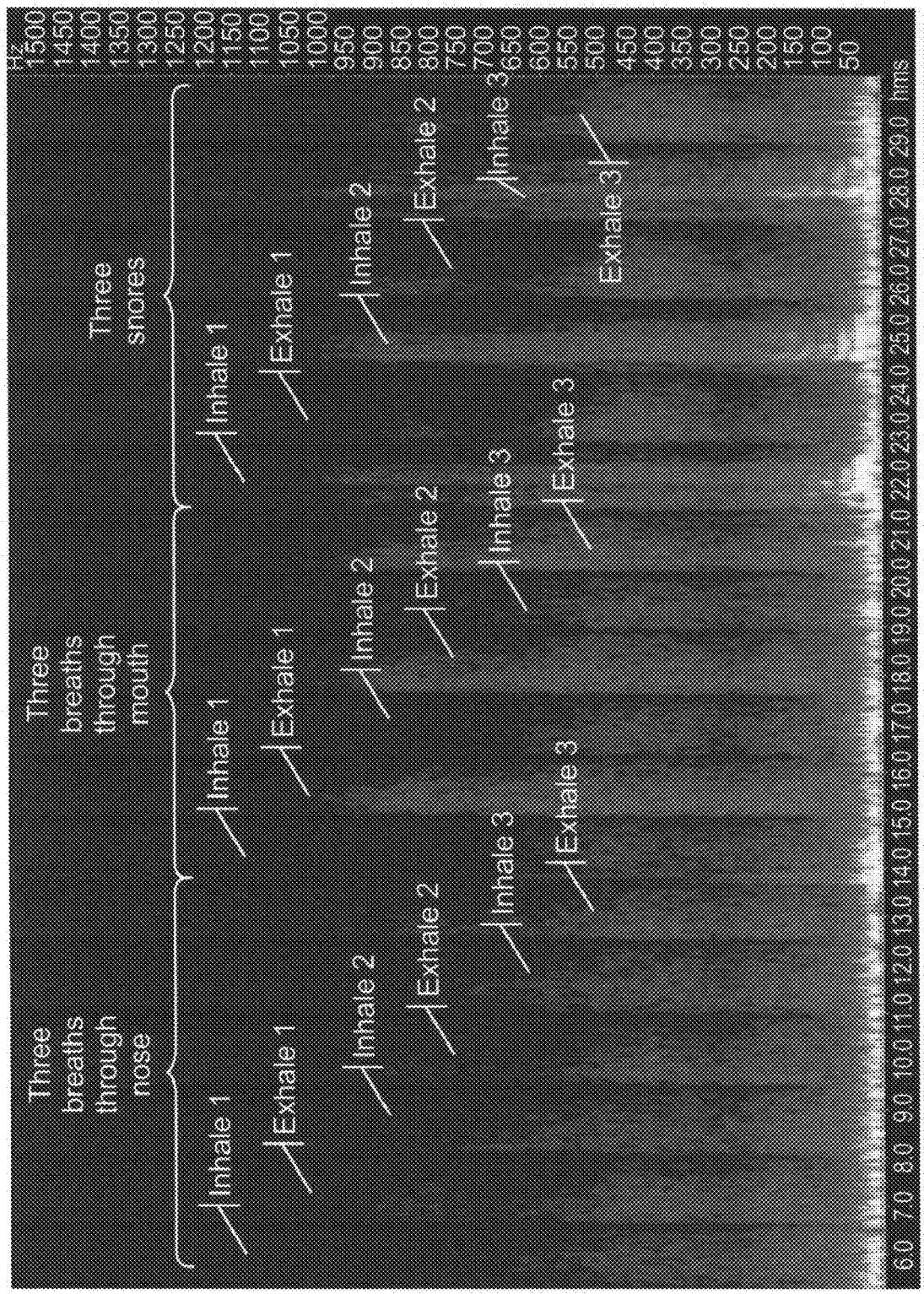
Figure 13:
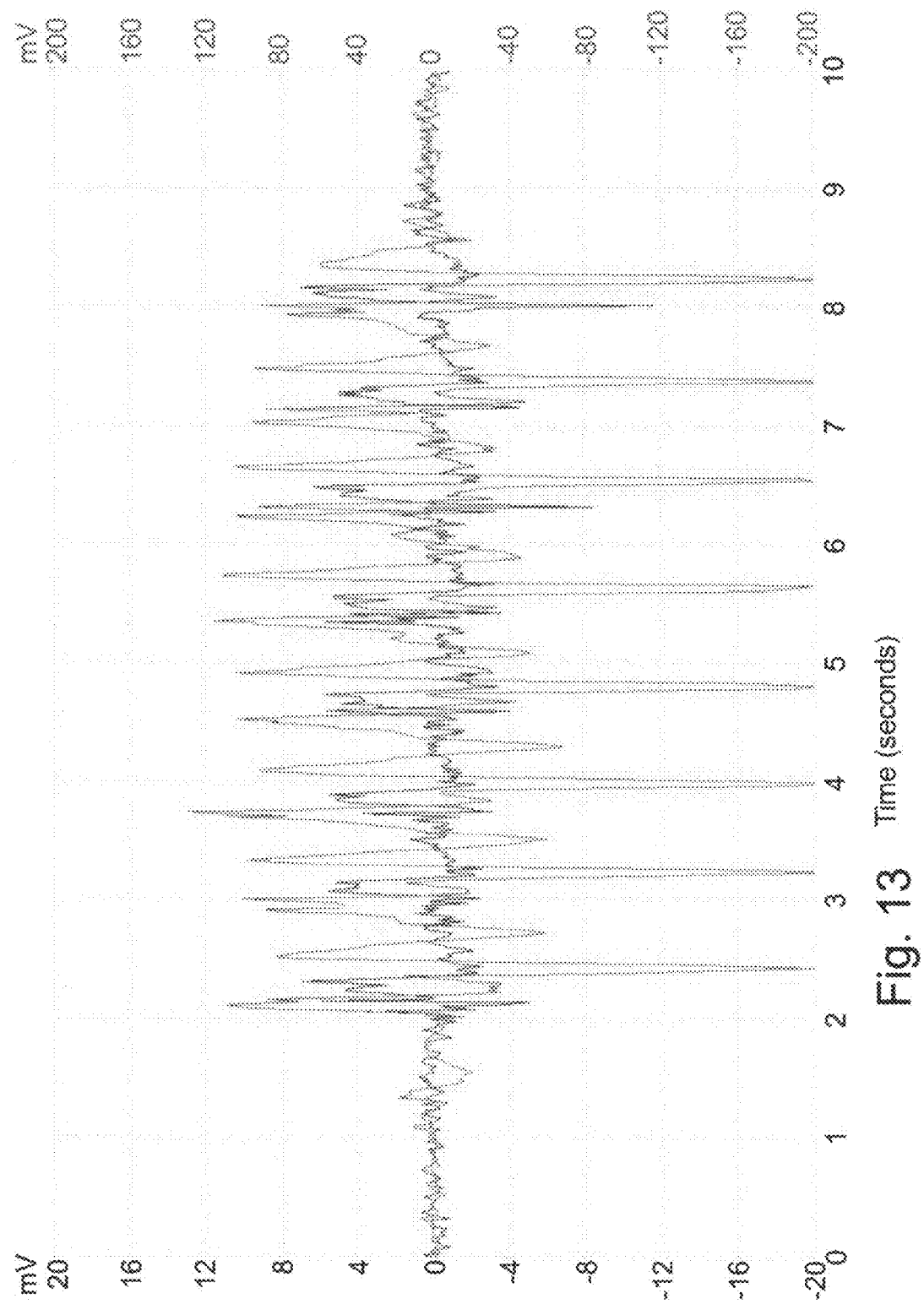
Figure 14:
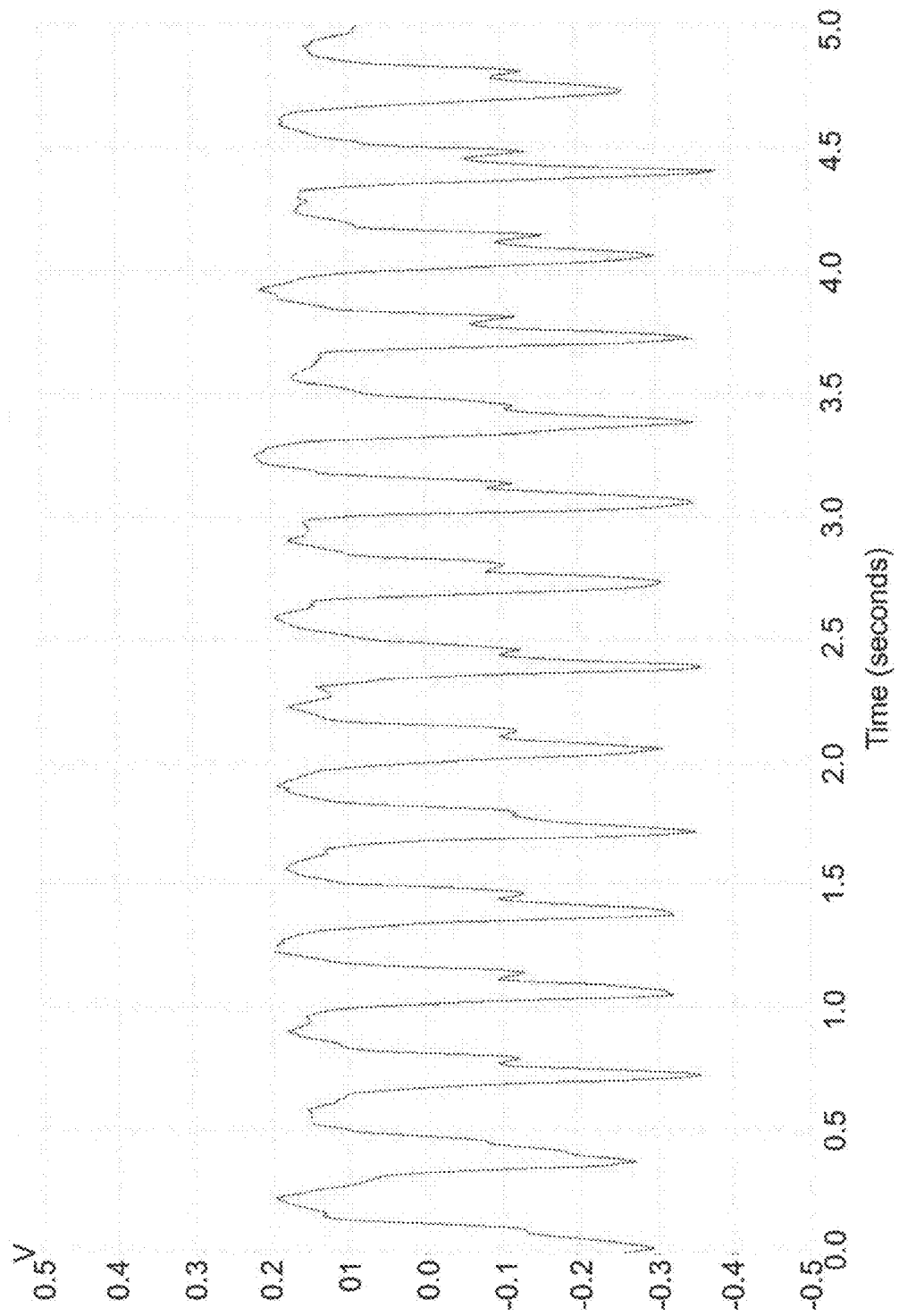

FIGS. 1a-d illustrate several embodiments of the system of the present invention being worn in or around the ear and communicating with a processing unit via wired or wireless connection;

FIG. 2 schematically illustrates the hardware components of one embodiment of a diet control system constructed according to the teachings of the present invention;

FIG. 3 is a flow chart illustrating an eating microstructure model;

FIG. 4 is a data flow diagram of the software components of the system of the present invention;

FIG. 5 is a flow chart diagram showing various layers of the system network as an integrated system;

FIG. 6 illustrates an embodiment of the present system in which an ear piece sends data or sound to a belt unit through wired or wireless communication;

FIG. 7 illustrates an embodiment of the present system in which an ear piece and a belt unit can engage in two-way communication of data and/or sound through wired or wireless communication;

FIG. 8 illustrates hardware components of a wireless transponder and a user interface unit;

FIG. 9 illustrates the synchronization and automatic calibration of transponder data utilized by the system depicted in FIG. 8;

FIG. 10 is a captured screen image of a sound sequence manually labeled and analyzed for eating microstructure events;

FIG. 11 is a time trace of the acoustic energy generated by the heart as detected by a bone conduction microphone in the ear of a human subject;

FIG. 12 is a power spectrum of breathing sounds as detected by a bone conduction microphone in the ear of a human subject;

FIG. 13 is a trace of accelerometer and microphone signals of chewing activity; and FIG. 14 is a trace of jogging activity as detected by a head-mounted microphone.

DESCRIPTION OF THE PREFERRED EMBODIMENTS

The present invention is of a system and method which can be used to monitor and optionally modify a behavior of a subject. Specifically, the present invention can be used to monitor an eating behavior of a subject and provide real-time feedback for modifying such behavior.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Numerous approaches for modifying eating habits are known in the art. Although some benefits can be gained from using such approaches, none provide an ideal diet control solution as is evidenced by the growing need for new solutions for treating eating disorders such as obesity or anorexia.

Real-time feedback based on the microstructure of eating holds promise as a new tool for the behavioral modification of eating. Although research in this area has been hampered by the unavailability of analytical monitoring systems that can be used during the course of a person's daily life (Bellisle, F., B. Guy-Grand, et al. "Chewing and swallowing as indices of the stimulation to eat during meals in humans: effects revealed by the edogram method and video recordings." Neurosci Biobehav Rev 24(2): 223-8.), laboratory and clinical studies suggest the ability for achieving weight control by using eating microstructure events.

Studies have hinted at the benefits of monitoring and modifying consumption patterns.

For example, a 1985 study by Stellar and Shrager demonstrated that over a year or more, the number of swallows on any given day correlated more highly with weight gain on the following day than did user-derived estimates of caloric intake. ["Chews and swallows and the microstructure of eating." Am J Clin Nutr 42(5 Suppl): 973-82].

In addition, studies have also correlated between consumption rate and patterns and caloric intake. For example, in 1977 Meyer and Pudel demonstrated that non-obese persons regularly slow their rate of eating during the course of a twenty minute test meal, while obese persons tend not to do so. ["Experimental feeding in man: a behavioral approach to obesity." Psychosom Med 39(3): 153-7]; in 1972 Stuart and Davis demonstrated that smaller bites may result in slower ingestion rates. (Slim chance in a fat world: behavioral control of obesity. Illinois, Research Press); in 1984, Clifton et al. demonstrated that pausing between bites may lead to reduced meal size. ["Feeding rate and meal patterns in the laboratory rat." Physiol Behav 32(3): 369-74]; in 1980, Kaplan demonstrated that eating faster results in higher consumption. ["Eating style of obese and non-obese males." Psychosom Med 42(6): 529-38]; in 1966 Jordan et al. showed that the degree of hunger determines the initial rate of ingestion. ("Direct measurement of food intake in man: a method for the objective study of eating behavior." Psychosom Med 28: 836-842); in 1977 Meyer and Pudel postulated that having obese people slow down may reduce consumption ["Experimental feeding in man: a behavioral approach to obesity." Psychosom Med 39(3): 153-7]; in 1989 Spiegel et al. demonstrated that avoiding prolonged periods of non-eating that are followed by eating highly preferred foods reduces consumption. ["Responses of lean and obese subjects to preloads, deprivation, and palatability." Appetite 13(1): 45-69]; in 2000, Spiegel et al. demonstrated that obese people eat faster than people who are not obese, eat more food and more energy dense food, eat desert earlier then non-obese people and thus, by deferring or avoiding desert, consumption of obese people should will drop ["Rate of intake, bites, and chews—the interpretation of lean-obese differences." Neurosci Biobehav Rev 24(2): 229-37]; in 2000, Bellisle et al showed that eating rate increases with food that tastes good ["Chewing and swallowing as indices of the stimulation to eat during meals in humans: effects revealed by the edogram method and video recordings." Neurosci Biobehav Rev 24(2): 223-8]; in 1982 Kissileff and Thornton showed that effecting behavior at the start of a meal may determine how the rest of a meal is eaten ["Facilitation and inhibition in the cumulative food intake curve in man" Changing concepts of the nervous system. A. J. Morrison and P. Strick. New York, Academic Press: 585-607); finally, in 1966, Jordan et al. demonstrated that the volume of material ingested just prior to a meal ("pre-load") matters more than the caloric density of the pre-load, therefore, drinking lots of water 15 minutes before a meal will reduce consumption ("Direct measurement of food intake in man: a method for the objective study of eating behavior." Psychosom Med 28: 836-842).

These representative relationships between eating microstructure events and weight disorders prompted the present inventors to hypothesize that real-time biofeedback that is based on eating microstructure events could be utilized to monitor and modify human behavior and in particular eating behavior. As is shown in the Examples section which follows, the present inventors have demonstrated that eating microstructure events can indeed be utilized to accurately monitor the caloric intake of an individual.

While reducing the present invention to practice, the present inventors devised an approach which can be used to monitor a behavior (e.g. eating behavior) of a subject and provide real time feedback for altering such behavior (e.g. alerting the subject when they are eating more than allowed by their diet plan or more than is required to maintain their desired weight). As is described herein, such an approach can be embodied by a system which can be worn by the user in a comfortable and concealed location on the body, or implanted subcutaneously by a simple, low-risk procedure.

Thus, according to one aspect of the present invention there is provided a method of monitoring and optionally modifying a behavior of a subject. The terms "subject" and "user" are interchangeably used herein to refer to a mammal, preferably a human.

Any behavior which can be defined through a set of detectable activities can be monitored by the present system. Examples of behaviors include, eating behavior, or behavior associated with a psychological or a physiological condition, exercising, stress and the like, further description of such behaviors is provided hereinbelow.

Since such behaviors and others are typically characterized by a set of detectable activities (e.g. eating—chewing swallowing etc; stress—heart rate, breathing patterns, sweating etc), monitoring and processing such activities can be utilized to qualify a behavior.

The method is effected by monitoring activities related to a behavior and processing monitored information to thereby generate activity related data or signatures which can be used to qualify the behavior.

As used herein, the phrase "activity related signature" refers to a specific feature set, sequence of features, hidden Markov models, numerical values, graphical or image forms which are or can be attributed to a specific activity.

Although such a method can be practiced using any combination of software and hardware components, monitoring and modifying of a behavior according to the teachings of the present invention is preferably effected using a dedicated user-operable system.

To monitor such activities, the system of the present invention includes a sensor unit mountable on or in a body region of the subject. The sensor is selected capable of sensing mechanical (e.g. jaw motion), thermal (e.g. body temperature), electrical (e.g. EKG or EMG) or acoustic activities. Acoustic activity is preferably, non-verbal (i.e. does not result from vocal chord vibrations) acoustic energy at a frequency of 0.001 Hz to 100 kHz, which is generated from mechanically-induced vibrations or motion. Further description of activities and suitable sensors for monitoring such activities is provided hereinbelow.

Although the data sensed by the sensor of the present invention can be used to qualify a behavior without any further processing (further described hereinbelow), the system of the present invention preferably further includes a processing unit which is capable of processing the data sensed by the sensor and deriving an activity related signature therefrom.

Processing of activity related signatures generated by the present system enables qualification of activities and thus behavior and enables real-time monitoring and modification of such behavior. The Examples section which follows provides examples of activity related signatures as generated according to the teachings of the present invention.

The system of the present invention can be used to monitor and modify overeating and thus be used for diet control. The system can also be used to monitor and modify behaviors associated with eating disorders such as bulimia and anorexia, as well as to other behaviors including snoring, sleep apnea, bruxism, smoking, alcohol consumption, drug addiction, exercise and physical training, stuttering, panic disorders, attention deficit, hyperactivity disorders, or other disorders that have unique physiological, sound or motion characteristics (i.e. activities) that can be identified and monitored.

According to a preferred embodiment of the present invention, the system for monitoring and optionally modifying a behavior of a subject is utilized to capture and process eating activities in order to qualify and optionally modify (via feedback) an eating behavior of the subject.

The system comprises three sub-systems, a food ingestion detection subsystem sensitive to ingestion of fluids (liquids and gasses) and solids, a data gathering/processing subsystem, and a user interface. All or at least a portion of these subsystems are integrated into a self-contained package that can be worn by or implanted in the body of the user. An optional caloric expenditure measurement unit for determining the full energy balance of the user may also be included.

The food ingestion detection subsystem includes one or more sensors for detecting sound, movement, density, light, or other conditions associated with a particular activity. Sensors for sensing the chemical environment in the mouth cavity saliva pH etc, can also be used.

Such sensors can be on the surface of the skin, in the mouth, implanted subcutaneously, or implanted completely internal to the body. The sensors can be powered using an internal power source such as a battery, capacitor or fuel cell, extract power from the temperature differential between the body and the surrounding air such as described by way of example in U.S. Pat. No. 6,640,137 Biothermal Power Source for Implantable Systems, extract power from the motion of the user such as the mechanism in the Seiko Kinetic watch, winding of a spring, ambient solar power or indoor lighting, receive power through a wire from an external source, or receive power wirelessly from an external source such as magnetic inductance, electrical inductance, radio, microwave, ultrasound energy, or ambient RF energy prevalent in urban areas. Excess energy can be stored in a rechargeable or disposable battery, capacitor, or mechanical spring. The sensors can be powered parasitically from a connection to an external system such as a cellular phone or computer. The sensors can be charged by simply touching them to another object containing an electrical potential. The sensors can be powered by a coil and rectifier that generate DC power from transmitted RF signals generated by the system or present in the system environment.

Acoustic energy generated by chewing, swallowing, biting, sipping, drinking, teeth grinding, teeth clicking, tongue clicking, tongue movement, jaw muscles or jaw bone movement, spitting, clearing of the throat, coughing, sneezing, snoring, breathing rate, breathing depth, nature of the breath, heart beat, digestion, motility to or through the intestines, tooth brushing, smoking, screaming, user's voice or speech, other user generated sounds, and ambient noises in the user's immediate surroundings can be monitored through one or more sensors (e.g. microphones) positioned in or around the ear area, on the skull, neck, throat, chest, back or abdomen regions. The preferred area allows for such sounds to be analyzed in order to determine the nature of the bolus swallowed (type of food, number of chews, hard versus soft chews, crunchy versus soft food, ingestion of liquid etc.). Microphones in different positions or orientations can be tuned to detect sounds originating within the user's body as opposed to ambient sounds surrounding the user. Software can be used to select which microphone is given priority for data collection and analysis based on the situation. Each microphone can be optimized to receive a specific range of sound frequencies corresponding to the signal to be measured. The sensing element can be designed to be sensitive to a wide range of frequencies of the acoustic energy generated in the head region, ranging from approximately 0.001 hertz up to approximately 100 kilohertz. The sensing element can be sensitive to just a narrow range of frequencies and a multiplicity of sensing elements used to cover a broader range of frequencies. The sensing element can receive the acoustic energy via air transmission, tissue or bone conduction.

The microphone can be fabricated from electret, piezo, silicon (MEMS), or other materials and technologies known in the art. A mechanical membrane acting as an acoustic lens may increase the sensitivity or directionality of the microphone.

The swallowing event can be detected indirectly, such as from the temporary and periodic cessation of breathing, chewing, or other eating sounds and patterns.

The system can pick up sounds anywhere from the throat or neck region upwards with a microphone. The system may also have a sound tube to convey the sound to a sound processing unit elsewhere on the body. Such a sound tube can be, by way of example, a hollow plastic tube connected to a mounting means in the ear region and a sensing means such as a microphone in proximity to the sound processing unit.

The ambient noise or the noise of the speaker can be cancelled out from the microphone input using passive and active means such as a focusing diaphragm, acoustic shielding of the sound sensor, dual diaphragm microphone designs, ambient sound sensor electronically coupled to the sound sensor, ambient sound sensor digitized separately and subtracted in software from the sound sensor, or any other means of noise cancellation known in the art.

The sound sensor may transmit information with 100% duty cycle continuously or only when an eating event is detected. When not transmitting sounds, the microphone and the associated electronics can be in standby mode to conserve power.

The frequency response may be limited to the spectrum required to discriminate the signal sounds and, if the voice input/output functions described later are enabled, to pick up intelligible human speech.

The system can also register sounds of defecation and thereby determine the timing and nature of these activities for the purpose of diagnosing and alerting to situations of constipation, diarrhea or excessive laxative use. These sounds can be registered directly or inferred through respiratory changes such as "holding one's breath" while defecating. Such respiratory changes can be detected through any of the means described below, including motion of the chest wall or sound analysis.

The system can detect the external and/or the intra-body sounds generated during urination. By measuring the duration and frequency of urination throughout the day, the system can keep track of the hydration level of the user. If necessary, the system can prompt the user to drink additional fluids as described later.

A swallowing event can alternatively be inferred from the temporary cessation of breathing ("swallow apnea"). This swallow apnea can be measured through physical means (i.e. chest strap), induction plethysmography, sound analysis, by monitoring airflow either inside or outside the airways, or by any other means known in the art.

An article by Moussavi et al. (Computerised acoustical respiratory phase detection without airflow measurement, Med Biol Eng Comput. 2000 March; 38(2):198-203), describes suitable locations and methods for listening to the correlation of breathing and swallowing sounds. By monitoring breathing, the system can also detect sleep apnea events and remedy disorders such as snoring with the same or a similar system.

By monitoring breathing, the present system can also detect abnormal breathing rate or breathing depth that may be the result of stress. By communicating with the user through any of the approaches described hereinbelow, the system can pace the individual into a relaxing breathing pattern. Alternatively, the user can manually activate this "breathing pacing" function any time he or she desires to do relaxation exercises. In an alternative embodiment for stress management, the system would detect whether a user's heart beat was chaotic or coherent and coach the user into coherence using biofeedback techniques.

The system of the present invention can alternatively or additionally include an elastic chew detection pad mounted on the lower molar which is contacted by the upper molar when the upper or lower teeth are close together and lack of contact is detected when the teeth are apart in a normal chewing pattern. The elastic chew detection pad can be fabricated from a few basic elements: a combination piezo detector and sound transducer, an RF transmitter/receiver, and an optional power source such as a battery. The chew sensor can also detect chews by measuring singly or in combination the motion, friction, strain, sheer forces, oximetry, tissue color, temperature, electrical resistance, capacitance, or pressure between the tooth and the cheek of the individual.

Food being chewed can cause a displacement or pressure on the chew sensor and generate a signal instead of, or in addition to, the teeth themselves. Alternatively, two passive elements can be attached to an upper and lower tooth and when the teeth are in proximity, one element affects a physical or electrical property of another. When processed internally or when queried by an external transponder system, the chew can be detected.

One example of such an embodiment can be an electrical circuit, such as, for example, a resonant audio or radio frequency circuit which is positioned in the top tooth and whose resonant frequency is affected by the presence of an element positioned in the bottom tooth. The external scanner unit queries and/or powers the circuit in the top sensor much like a passive RFID tag with the additional information transferred by the circuit in the top tooth indicating the proximity of the bottom tooth to the top tooth.

The external unit can power the system using techniques described elsewhere in this application. Alternatively, the force of biting can itself generate enough electricity to power the system or cause a burst of electromagnetic energy or a change or phase in a circuit that is detected by an external unit. This would allow a body-mounted system to be passive and not require a battery. Furthermore, the body-mounted system when embodied in a dental appliance can optionally have the necessary memory buffer and processing to store and process the chew pattern for downloading into an external unit in real time or batch mode.

The system can also measure the user's heart rate, heart rate coherence, breathing rate or breathing depth patterns or galvanic skin response to assess their stress, fear or anger level and then provide feedback to reduce the stress by, for example, talking the user through breathing exercises. This could be useful in proactively reducing violent activity and impulsive behavior. The galvanic skin response can also be correlated to the general mood of the user and the system can provide encouraging or funny verbal feedback to improve the user's mood.

One or more of the user's limbs can be fitted with accelerometers or induction systems which allow the location of the limb in space to be monitored at all times. The system can then detect movement of, for example, the hand to the mouth as a measurement of the quantity of food or liquid consumed.

The time and force of each chew can be recorded using external electromyographic (EMG) recording from the muscles involved in chewing. For example, swallowing events, their intensity and duration, can be detected using external electromyographic recording from the muscles involves in swallowing, including but not limited to submental muscle group and the tongue muscle, as described in Vaiman M, Segal S, Eviatar E, Surface electromyographic studies of swallowing in normal children, age 4-12 years; Int J Pediatr Otorhinolaryngol. January 2004; 68(1):65-73, which is incorporated herein by reference. Electrodes for the EMG system can be made from transparent material and unobtrusive so they are barely visible.

The passage and size of food in the esophagus can be detected using electrical impedance measurements or electrical impedance tomography (EIT). Further, electroglottography (EGG) is a technique used to register laryngeal behavior indirectly by a measuring the change in electrical impedance across the throat. Chewing and swallowing can also be detected using this technique. Such a technique is described at www.ims.uni-stuttgart.de/phonetik/EGG/pagee1.htm.

The passage of food in the esophagus can also be detected using one, two or three dimensional ultrasound measurements in direct or Doppler mode. The passage of a bolus of solid or liquid nature will register as a change of density across the esophagus, with different densities based on the composition of the bolus.

Chewing, swallowing or stomach volume can alternatively be detected using one or more position sensors implanted on the inside or outside surfaces of the mouth cavity, esophagus or stomach. For example, one could implant one or more small sensors in these organs endoscopically and inductively measure their position in space relative to a reference and hence the volume of the organ between them.

A sensor positioned inside the mouth can also be used to detect changes to the mouth cavity when food is introduced, such as mouth cavity volume changes during chewing and swallowing, motion of the tongue or mouth wall, micro temperature change measurements, glucose content, or electrical impedance changes caused by the food.

Stomach volume measurement can also be used to detect food intake. Stomach volume can be measured, for example, by using electrical impedance tomography or ultrasound techniques.

Swallowing or chewing can be detected using one or more accelerometers or vibration detectors placed on the skull, neck, ear, jaw or throat areas. Furthermore, breathing, and therefore swallow apnea, can be measured using one or more accelerometers or vibration detectors placed on the chest area.

Chewing events can also be sensed via mechanical deformation of the ear canal that occurs during chewing. One advantage of this signal is that the deformation is strongest when eating, and less strong when talking. The deformations of the ear canal can be detected using microphones or mechanical sensors such as accelerometer, piezo or strain gage technology known in the art, and/or changes in volume or pressure of a space-filling element in the ear canal, and/or optical means. The system can be designed with flexible members to universally fit into all ear canals, or a limited number of standard sizes to fit most ear canals, or lastly custom fit for each individual based on his or her ear canal geometry. The signal processing and power aspects of this technology can be from any of those described in other sections of this application.

Alternatively, chewing events can be detected via a passive wireless strain monitoring sensor which is inserted into the ear canal. Deformation of the ear canal will cause a capacitance change of the strain monitoring circuit; the change of the capacitance causes a change of the filtering frequency of a filter circuit in the ear canal. Measurement of the frequency of a radio wave passed through the filter circuit enables measurement of the strain of the ear canal and hence detection of chewing action in a wireless fashion with a passive sensor in the ear canal. A belt or neck mounted unit can transmit at, for example, 915 MHz and lock onto the passive ear unit reflector with a pseudo-random number generated code. The system could modulate the amplitude or clock frequency of the pseudo-random number generator to convey a code and information.

A chewing sensor can sit in, on top, between or around one or more teeth and detect biting and chewing events and relay this information outside of the oral cavity through a wired or wireless connection to an external system that does the data processing and provides the user with feedback. The system, or its mounting bracket, can be attached to one or more teeth using adhesives known in the art for the adhesion to teeth of dental appliances such as brackets for braces, or alternatively a clip or tensile element that secures between or around the teeth. The chewing sensor can be mounted, in one embodiment, on the outside surface of a lower molar and the overhang of the upper molar when the mouth is closed will impinge on the chewing sensor and generate a signal. An example of such a sensor would be a piezoelectric element. The same piezoelectric element may be the chew detector and also perform the functions of a sound transducer to provide the user with sound or verbal feedback through bone conduction acoustic energy transferred through the tooth. U.S. Pat. No. 5,447,489 incorporated herein as a reference describes conveying sound to the user with a dental appliance via bone conduction through the teeth.

In an alternative embodiment a proximity sensor such as a microswitch, Hall-effect transistor, inductive sensors, reluctance measuring sensor, capacitor, ultrasonic proximity sensor, magnetic field generator, magnetic reed switch, giant magnetoresistance (GMR) sensing element, or any other proximity sensor known in the art is mounted on the top molar and if necessary a second element, such as a capacitor plate, mechanical impingement surface, magnet, metallic, or paramagnetic component, on the corresponding lower molar. The system can buzz loudly or otherwise alert the user if it becomes detached from the tooth by accident, thus preventing it from being accidentally swallowed. In any eventuality, the system would not cause any harm if swallowed accidentally by the user. A diode or other protective circuit can prevent current from flowing out of the system to the surrounding tissue while allowing an electric charge supplied from outside the system to recharge the on-board battery. The external system can be a dedicated computing means or a cellular phone or hand held computing system. The signal emitted by the chewing sensor can be received directly by such a system. The sensor in the mouth can be permanent, partially removable (leaving a mounting means in place) or fully removable. The system could be charged and/or data exchanged with an external control unit while in the mouth or when removed and placed in a charging and/or data exchange unit. The system could be disposable and simply removed and disposed of after a set amount of time, and the data logged in the system collected by and external control unit prior to the disposal. The sensor in the mouth can be powered by a disposable or rechargeable battery or capacitor or be powered by the biting force of the user. Alternatively, the sensor can be powered by ions conducted through saliva using electrochemically-active electrodes on the system or by ingested glucose or intrinsic glucose in the saliva. For example, a material containing copper chloride and sandwiched between strips of magnesium and copper will generate electricity when exposed to fluids containing ions, such as saliva.

The above described sensors can be combined in an integrated system to increase the reliability or precision of the food volume monitoring.

The system of the present invention can preferably gather data from one or more of the sensors described above continuously, whenever a sensor detects such event, or when the user indicates the occurrence of an eating event. Any of the sensor's output may be interpreted by a universal algorithm, by asking the user to perform certain calibration tasks (e.g., eat food of known weight and consistency, swallow water, etc.) or by monitoring the patterns over time and adjusting the interpretation algorithms.

The present system can gather information about the user's weight by communicating through a wired or wireless connection with a body mass measuring system (such as a traditional weighing scale), a body fat measuring system (such as a body fat composition scale, hand-held fat detection system, or calipers), a specially designed garment or other physical measurement of one or more body parts; or a continuous body weight measuring means, such as load sensors placed in the shoes of the user or the seat of the user's vehicle.

The system of the present invention can detect the beginning of a feeding event and time a meal by receiving a signal from a sensor described above or by manual triggering by the user. The system can provide the user with feedback after a certain amount of time has elapsed, thereby limiting the duration of the meal. This time period can be set based on historical eating times collected by the system during its use by the user. Since the present system can store information regarding normal meal times, between-meal snacks or binge eating can be detected and discouraged.

Solid or semisolid food are chewed longer and typically take 4-8 seconds to pass through the esophagus. Very soft foods or liquids are chewed less and take only about 1 second to pass through the esophagus. This difference in the speed with which various foods pass through the esophagus provides a detectable difference to allow the system to infer the volume and contents of the swallowed food. The volume and consistency of the swallowed contents can be inferred by the timing, intensity, velocity or other characteristic features of the detected chewing and swallowing event. Thus for example, the system can discriminate between the swallowing of saliva, thin liquids such as water, thick liquids or solid foods. The caloric content of each type of swallow can therefore be inferred and roughly calculated.

The system can discriminate between an "empty" swallow of saliva only and a "full" swallow of food by discriminating among variables such as, for example, the timing and intensity of the swallowing event, the respiratory patterns, and the lack or presence of chewing or biting before and after the swallow event.

The system can detect the eating patterns of the user over time, thereby building a database of ingestion behavior and "learning" and customizing the performance of the system to the user. The system can then alert the user or a third party upon detection of eating patterns that are outside the norm, such as binge eating, weekday eating versus weekend eating, eating patterns around the holiday seasons, or skipped meals.

The data generated by the system for each subject can be integrated and/or aggregated into a flat or relational database containing the behavior related activity signatures collected from a plurality of subjects over a time period. Such a database can contain proprietary data, publicly available data, anonymously collected data, and/or data collected with subject identification information. Data could be collected at a variety of levels, from raw recordings of sensor data, processed sensor data, activity-related signatures, or high-level behavioral data. Such a database would be useful for establishing norms, averages, trends, classifications, calibrations, historical behaviors, reference sets, training data, statistical tests, clinical trials, targeted marketing, third party interventions, and relative scores in a stand alone manner as pure data or as an integral part of the system used by individual subjects. Such a database can be cross referenced to other databases. By way of example, a database of the physical activity patterns or ingestion patterns of many subjects can be cross referenced to a database of their health, medical, exercise, drug use and/or weight records. Unexpected relationships are likely to emerge from an analysis of such a database. For example, a drug company doing a clinical trial of a drug may find it useful to measure the ingestion behavior of the patients in the trial to detect any changes of eating or drinking behavior of the patients either as a result of taking the drug or as a side effect. By way of a second example, an aggregated database of the ingestion related motion or acoustic energy patterns detected for a plurality of users can be used to train the algorithms used to convert these patterns into classifications of ingestion behaviors. Additionally, such a database can be used to let a subject know where he or she is performing relative to other users of the system.

The system may be "food and diet agnostic" and thus will be operable with different food types and diet plans (e.g. those that prefer high protein versus high carbohydrate versus high fat foods). The system may even adapt to changing eating habits of individual users throughout the day or over the course of weeks or months by learning the specific food preferences of the user and "closing the loop" using one or more of the body mass detection means described above. If the user changes their food preference over time, towards higher energy density foods for example, the system can recognize that fewer swallows are required to reach the caloric intake budget because the weight of the individual will be higher for a given number of swallows. Or, as another example, if the person is very physically active, the system can increase the caloric budget to maintain the desired energy balance.

The system may further be adapted to detect patterns in body mass or fat content measurements by one of the means described above and use such patterns to calibrate, with or without user input, the allowed caloric input based on desired weight targets and time periods.

The system can also calculate stomach volume and help insure it does not exceed a maximum volume thus preventing the stomach from over-expanding and thereby restoring the sensitivity of the innate satiation mechanism.

The system can be pre-programmed at the factory, at the point of sale or at home to require no user intervention other than wearing the system in a pre-set weight reduction or weight maintenance mode. The system can communicate directly with the internet, a personal computer, laptop computer, pocket computer, personal digital assistant, cell phone, pager, watch, a dedicated control panel on the system or a dedicated external system for programming the system and/or the physical activity monitor. The user can program the system by touching one or more data-input buttons or dials on the system. Alternatively, the system incorporates voice-recognition capability so that the user can program the system by talking to it.

The system may illicit feedback or programming instructions from the user by way of audio queries which require yes/no responses with a distinctive sound such as snapping of the fingers, clicking the teeth or clicking the tongue on the roof of the mouth. The number of clicks may elicit different responses by the system.

The user may prompt the system for information in a similar manner. The system may then report information such as level of compliance, goal attainment, etc. In this way, the system can be highly interactive and fun to use.

The system can be set by the user to issue occasional summary reports or real-time messages or stimuli before, during or after a meal. The messages or stimuli can be set by the user or a third party to be anything from gentle reminders to un-ignorable in terms of their intensity. The system can be programmed by the user or a third party to not be controllable by the user for a set period of time or until certain events or parameters occur. This could include not having the user be able to turn off the machine at all, or more than a set number of times per day.

The system can monitor the user's compliance with the proper and consistent use of the system and with the user's compliance with the behavioral guidelines and alarms emitted by the system. This compliance data can be made available to the user and/or a third party through, for example, the internet or other data distribution means.

The system will be able to handle exceptions and deal with them intelligently. For example, if the user did not wear or turn on the system for a set period of time, the system can beep or otherwise alert the user until the system is put on by the user. Since the system will be able to keep track of time and a usage history, it can use average caloric consumption values from previous usage data for the skipped measurements. The system will detect a skipped meal by not detecting swallows at the appropriate time and then carry forward the unused caloric budget to the next meal. The system can detect an increase in physical activity and increase the caloric budget for that same day.

The system of the present invention preferably can be configured to communicate directly with the internet, a personal computer, laptop computer, pocket computer, personal digital assistant, cell phone, pager, watch, a dedicated control panel on the system, or a dedicated external system in order to provide audio or visual feedback, summary statistics and trends, the unprocessed or processed data collected by the chew or swallow sensors and/or the caloric expenditure monitor.

The system can produce a coded sound audible to the user. The system can produce synthesized or prerecorded speech messages to the user through a speaker, an in-the-ear speaker, or through bone conduction technology.

Bone conduction technology could relay sound signals or synthesized voice messages through the upper chest, collar, neck, jaw, finger or cranial bones to the ear so only the user can hear the system. Bone conduction speakers can be made from piezoelectric materials, magnetic transducers, magnetic vibration transducers, floating mass transducer, or other transducers known in the art.

A bone conduction speaker will not generate significant sound to the outside world, and therefore the microphone component for picking up the user's voice, internal cranial sounds and/or ambient sounds in the user's environment usually will not need to cancel out the feedback of the speaker sounds. This should enable full duplex communication with a minimum of signal processing for applications such as cell phone headsets for example, even in the case where the speaker and microphone are co-located or in close physical proximity. In another embodiment, time-division duplex techniques can be used to separate the microphone input from the speaker output.

As single transducer can act as both a speaker and microphone in that the transducer generates electricity from sound or bone vibrations and the same transducer also generates sound or bone vibrations from an electrical signal. Software and electronics can drive the transducer in either microphone or speaker mode. The software and electronics could also deconvolute the signal to allow simultaneous use of the transducer in both microphone and speaker modes.

The system of the present invention can wirelessly trigger the release of a chemical substance, such as for example a substance contained in an intelligent micro-fabricated drug delivery system (e.g. www.mchips.com) that resides in the mouth cavity and is capable of creating a temporary bad taste or slight nausea. Alternatively, the feedback can be positive and the chemical can cause a pleasant taste in the mouth.

A small amount of a chemical could be administered, for example via transdermal delivery or implanted drug depots, in either the context of a behavioral reward or a behavioral deterrent. The deterrents could be substances that range from highly noxious to mildly painful or just annoying. They would provide a disincentive to the behavior and Pavlovian conditioning against the behavior.

The following lists several possible chemicals whose release from the system could deter a behavior:

(i) Capsaicin—the "burning" chemical in chili peppers (and police pepper spray) delivery to get a burning sensation;

(ii) Niacin dietary supplement—causes flushing and/or itching;

(iii) Substance P—endogenous 'neurotransmitter' involved in pro-pain pathways;

(iv) Cinnamon (or concentrated extracts)—stimulates heat sensitive nerve receptors; and (v) Menthol or eucalyptol (or like)—stimulates sensitive nerve receptors.

The following lists several possible chemicals whose release from the system could reward a behavior:

(i) Opioids and/or amphetamines—directly block pain receptors;

(ii) Serotonin and/or melatonin—used for depression, anxiety, obsessive-compulsive disorder (OCD), give feeling of satiety;

(iii) Leptin—linked to satiety, directly to weight loss (weight homeostasis);

(iv) Dopamine (or related neurotransmitters)—linked to CNS reward centers, satiety, well-being; and (v) Tryptophan—naturally occurring essential amino acid; released from "warm milk at bedtime" effect; comfort or sleepiness.

The system of the present invention can release into the environment of the user stored substances that have pleasant, neutral or objectionable odors as positive, neutral or negative feedback to modify the behavior of choice. The strength of the smell can be constant or increase with the strength of the desired feedback. The smell compounds can be stored on the system or be stored in a separate system that is in communication with the diet aid system. Individual smell compounds can be combined to produce a composite smell. The user can calibrate the system regarding which smells he or she find pleasant, neutral or objectionable.

The system can release or command the release of chemical substances such as insulin or other hormone, enzyme or drug, thereby allowing correlated release of the substance with the ingestion of food or drink. The chemical substance can be released directly into the stomach, intestine, muscle tissue, peritoneum, lymph fluid, airways or bloodstream by a drug delivery system. The system can cause the release of a compound through the skin by any of the technologies known in the art. The system can compute the amount of food ingested and simply alert the user to inject a certain calculated amount of insulin or other drug prior, during or after a meal.

The system can produce a visual display of information for the user, using for example lights, symbols, graphics or numbers. The system can also vibrate a coded message to the user.

The system may electrically stimulate the user either using surface or implantable electrodes causing increasing discomfort or communicate to an implanted nerve stimulator or a gastric pacing or banding system that retards or accelerates stomach filling or emptying. Upon detection of overeating or misappropriate eating behavior, the system can first issue "warning signals" to the user such as an audible feedback. If the subject does not heed these warning and once preset limits of ingestion or too fast an ingestion rate have been reached, the system can then escalate the intervention and trigger an electrical stimulation or some other form of feedback that is un-ignorable.

The system of the present invention can further activate a mechanical impingement on the body, such as for example a pin-prick system, activation of an actuator or the fastening of a belt against the stomach or other body part of the user to make eating less enjoyable. The systems can mechanically or electrically stimulate sensitive points on or in the body, such as for example acupuncture points, to create a feeling of fullness, suppress appetite, induce nausea, or cause a pleasant sensation. By way of example, transcutaneous electrical nerve stimulation (TENS) techniques can be used for this purpose.

The system of the present invention can further induce nausea or an unpleasant sensation using ultrasonic and high frequency sound energies. One embodiment could utilize a miniaturized high frequency sound transducer as an integrated component of the device for eliciting slight nausea. Such a commercially available product is called "Sonic Nausea" and is available for purchase over the internet. The transducer can transmit the sound waves in the vicinity of the user or directly through the skin or into the ear or ear canal.

The system of the present invention can further be utilized as a "virtual lap band". A laparoscopic band ("lap-band") is one of the most common forms of weight loss surgery. A lap-band is a procedure in which a band is placed around the stomach or the lower esophagus. Band placement allows the obese person to feel full after eating only a small portion and to continuously lose weight. Eating too fast causes a very unpleasant feeling in the patient and the band prevents the ingested food from reaching the stomach too quickly. Lap-band does not control the type of food, or even the amount of food that a patient eats during the day. Its effectiveness, however, has been proven in practice. To create the virtual lap-band effect, the system of the present invention can detect eating activities by counting the bites, chews and/or swallows in each eating sequence and determine an eating behavior and volume of food intake at any given time and the volume in the stomach as described elsewhere in this patent. The system of the present invention can trigger feedback when preset eating rates or eating durations are exceeded. Such feedback can be in the form of, for example, nausea, pain or other forms of negative feedback using techniques described elsewhere in this patent. With this approach, the need for an expensive and intrusive surgery can be eliminated.

The system of the present invention can be prescribed for use by a subject by a health care or nutrition professional as part of a weight management program. The subject's compliance with a prescribed weight control plan can be monitored and encouraged by the device. The data collected by the device can be made available to the user and the health care or nutrition professional.

The system can be adjusted so that it cannot be turned off by the user without proper authorization or medical procedure, such as a code, special key or explanation of an implanted system.

The system can be part of a formal medical or diet plan where the system would collect data and transmit them in batch mode or in real time to a server or other data sharing mechanisms where a clinical specialist, doctor, nurse, dietician, friend, family member, other system users, or any other relevant third party can be alerted for possible intervention.

When utilized for such purpose, the system can employ any sensor capable of detecting ingestion activity (eating/drinking) and a data transfer unit (e.g. transmitter) for relaying (wirelessly or through a wired connection) sensed ingestion activity to the server or other data sharing mechanisms (examples of transmitters and transmission modes are provided elsewhere herein). The sensed ingestion activity can be transmitted without being preprocessed in which case it can represent a simple time and duration of ingestion, intensity and rate of ingestion, count of bites, chews, swallows, etc., over a time period. If desired, transmitted non-processed data, such as by way of example raw audio recordings of ingestion sounds, can be processed by the third party to derive activity related signatures etc.

Alternatively, the sensed data can be processed by a processing unit integrated into the system to derive activity related signatures and other relevant information. Such processed data can then be transmitted to the third party.

The system can be used to qualify or classify candidates for pharmaceutical or surgical procedures by monitoring eating patterns beforehand. For example, before qualifying for insurance reimbursement or a referral for bariatric surgery, a patient would submit the eating patterns as collected by this system to their caregiver for analysis and the risk and likely outcomes of the surgery can be simulated, analyzed, and predicted.

The system can provide positive feedback when the user stops eating at or below the caloric budget threshold using any of the means above.

The system can alert the user when not enough physical activity has been detected, thereby providing an incentive to exercise in the proper amount. Conversely, the system can provide positive feedback when enough physical activity has been detected.

The system can provide ongoing feedback as to where the person is relative to the caloric budget before during or after each meal or other period of time such as a day or week.

The system can proactively predict low blood sugar situations by detecting the time between meals relative to historical eating and activity patterns and alert the user to either eat or provide a preventive message to avoid binge eating that may be triggered by low blood sugar situations. Conversely, the system may proactively predict high blood sugar situations and warn the user to stop eating or take his or her insulin medication.

The system can issue "warning signals" prior to alerting the user with full force to allow for gradual cessation of eating. The system can generate appetite generating messages or sounds in order to encourage a person to eat or appetite suppressing messages or sounds in order to encourage a person to stop eating.

The system can detect eating rate and warn the user to slow down, allowing for natural satiation signals to build up and thereby allowing people to eat less.

The system can encourage the user to take smaller bites by detecting chewing time and intensity. Smaller bites will cause the user to eat slower and therefore eat less.

The system can issue "pre-emptive" signals or voice messages with psychological content, either positive or negative, before or during the meal to remind and encourage the person to eat less.

The system can act as a virtual personal eating and physical training coach, providing real time feedback and encouragement. Attention is given to the psychological aspects of the disorder being treated by this system. For example, after detecting a binge eating episode, the system will surmise that the user may be feeling disgusted, guilty and depressed by his or her actions, and the system will therefore issue encouraging and supportive remarks to ameliorate these feelings, much like a real psychological coach would do.

The invention further provides methods of controlling weight gain and/or encouraging weight loss. In one embodiment, the user can deposit a set amount of money or equivalent with the maker or seller of the device or an independent third party and earn back the money according to their performance relative to preset weight or behavioral goals as registered by the device. In a further aspect, the user can earn something of value from the maker or seller of the device or an independent third party according to their performance relative to preset weight or behavioral goals as registered by the device.

The system can be provided to the user free of charge or for a small fee and in exchange the user would be subject to merchandising or advertisement delivered in an audio format and personalized to the user and the user's immediate interests, needs and location based on the device's understanding of the user's current situation. For example the system can detect a user's presence next to a health club and given that the user is trying to lose weight, the system would broadcast an audio commercial about the benefits of that health club to that particular user while the user is walking by.

The system can have the feedback integrated into a video game where the reward for good weight-management behavior is that a character, virtual situation or score becomes more favorable to the user based on the success of the user modifying their behavior. The user could also compete among other similar users also represented by characters in the video game in a community of users, all competing to achieve a behavioral-modification goal and the actual performances of the players are visible to all the community members participating in the video game. This embodiment is likely to be popular with children fighting childhood obesity for example. The same competitive game concept and competition within or among teams can be used without the video game concept, but rather with a simple scoring and communication feedback system. Team members would have an incentive to encourage one another, and the system could be programmed to alert the rest of the team when one member deviate significantly from their behavioral modification plan. The other team members could then intervene in real time using the telephone, email, SMS, through the device itself, or in person, to encourage the individual to modify their behavior. This system therefore, facilitates a real-time support group to the user during the entire day.

The system could alert the user when another individual using such a device is in close proximity, thereby encouraging a sense of community among the users of the system.

The system can predict the current hunger level of the user based on historical eating patterns compared to the eating pattern of the present day. The system could either encourage the user to eat something to avoid a drop in blood sugar which could cause a binge eating episode later. Alternatively, the system could discourage the user to eat when they are not physiologically hungry, but rather bored or upset. In this case, the system could offer alternative activities or emotional support, either using internal feedback content, or by alerting a friend or family to the user's situation.

The system can have stored in its memory workout routines for physical exercise, such as by way of example, pre-programmed yoga instruction. The device can monitor the pulse, breathing activity and even position of the limbs of the user using wired or wireless position sensors and provide audio feedback regarding the exercise much as a personal trainer would. The device can pace the workout and the user can interact with the device during the exercise session, including reprogramming the device or the exercise plan before, during and after the workout with any of the programming means described elsewhere herein.

The system can output or communicate directly to the user summary statistics at regular intervals or upon demand, such as a user's weight, body mass index, the number of chews, swallows, calories consumed, activity levels during a given period, the rate of change of each, trends and distances to set goals.

The system can have a mute button or a standby mode if the user does not want for the system to interfere or bother the user during a certain period. The system can continue to collect data and defer the feedback to the user until the mute function is cancelled.

The system can be calibrated by simply being worn by the user for a period of time and then set manually or automatically to preset "diet modes" based on alerting the user to stop eating when the system senses the consumption of a preset or user-definable percentage of the food consumed during the calibration period. For example, after being worn by the user for a week or so, the system will have learned the eating habits of the user. The system then goes into "diet mode" automatically and alerts the user when he or she has eaten say 90% of each meal, thereby eliminating the last 10% of the total calories otherwise consumed by the user over the course of a day as determined by retrospective eating behavior. Relative to skipping meals altogether, to not eat the last 10% of the calories towards the end of a normal meal is easier, because some satiety has already set in. At some point the user becomes conditioned to this amount of food and may not even trigger the warning message, in which case the user can receive positive feedback from the system. Once the target weight is achieved, the system can go on "weight maintenance mode" which may require a reduction of only 0.1%-10% of the calories typically consumed by the user who would otherwise creep back up to a higher weight without the system.

The system can interact with the user and ask the user questions in real time, such as to inquire about the user's eating and activity plans for the day, and only then determine the right course of action. For example, the system can detect overeating and ask the user if he or she intends to perform physical activity later that day. If so, the system increases the calorie budget for the meal, and reminds the user later to work out. Furthermore, the device can alert the user how much exercise will be a required to work off the amount of food being ingested, partially as a deterrent to prevent the user from over-eating. This form of an interactive "relationship" between the user and the system will increase the user's emotional connection and desire to use the system.

The system can detect the user's mood by monitoring and analyzing the normal speech of the user and using a technique such as described, for example, in U.S. application Publication No. 2003/0055654 A1, or using any other technique known in the art. The system can then be able to respond and interact with the user in a manner much like a real person would. The system could also cheer the user up if the system sense sadness, or calm the user down if the system senses anger or stress. The system can also select and play music that fits or alters the user's mood either automatically or with the manual intervention of the user.

The system can share the user's moods and emotions with other people around the user. Such communication can be in the form of audible or visual signals emerging from the system itself or data exchange to a third party or with similar systems worn by other people.

The system can interact with the user in a polite manner by waiting until it hears a low level of ambient noise or user-generated noise before interacting with the user. For urgent matters, the system might wait within a set window of time, at which point the system may try and interact with the user regardless of the noise levels. The system can query the user using an audible and/or vibrational and/or visual signal to see if the user is agreeable to receive feedback or messages at that particular time. The user can respond to the system's query with a voice, sound, clicking of the teeth or other mechanical signal and the system would then provide feedback to the user.

The system can monitor or have communicated to it such factors as outside air temperature, ambient lighting conditions, humidity, barometric pressure, etc and through these factors be more attuned to the environment surrounding the user. The system can relay such information to the user verbally or visually.

The system can be adapted to operate in various languages, and may be user-adjustable to communicate in the language of the user.

The system can prompt the user before, during or after each feeding event to describe what he or she ate and recognize the user's speech. For example, the user can say the word "apple" before, during or after eating an apple and the system recognizes this word and then calculates the number of calories based on the number and volume of swallows registered by the system multiplied by the energy density of an average apple. Alternatively, the user can initiate the input of such information to the system before, during or after each eating event. The system can recognize all words spoken by the user, or a limited vocabulary of select menu items, or alternatively the user can select from a menu of items proposed by the system. Alternatively, in another embodiment, the system can incorporate or communicate with a chemical, taste or smell sensor that can classify or identify food types automatically based on their chemical compositions.

Table 1 below provides a caloric and nutritional content of a McDonald's hamburger as measured by the United States Department of Agriculture (USDA). A database for a wide variety of foods can be found on the USDA website (www.nal.usda.gov). The system of the present invention can store or have access to such a database for all common or user-specific foods in the form of a look-up table. The mass of food ingested per bite and per swallow varies from individual to individual. However, based on experimental data, the average bite size per individual remains relatively constant. So per individual user, the system can estimate the mass of ingested food based on counting the number of bites, chews and swallows. The system can be programmed to know the type of food being eaten either by deduction or user input, say in this example by the user saying "McDonald's hamburger" and the system recognizing the user's speech or prompting the user from a fixed menu of options. The system then uses the internal look up table for the food type being eaten and multiplies the caloric and nutritional density values by the actual mass ingested by the user to compute the caloric total or ingested mass of each of the nutritional components and report this back to the user or a third party in real time or summary form. The USDA database also includes a typical portion size. So if the user indicates to the system that they ate an entire McDonald's hamburger, for example, the system would not need to count the number of bites and chews, but would rather assume that the user consumed 105 grams of this food type based on its internal database of portion sizes. Mixed meals, consisting of a hamburger, fries, and soft drink for example, can be handled accordingly by estimating the average caloric content of solid versus liquid food and computing the ingested mass of each separately, or by using known portion sizes. In the future, foods and entire meals might be barcoded or otherwise encoded with nutritional values and portion sizes and this information loaded into the device to program it with what the user is about to eat.

TABLE 1

Nutritional content of a McDonald's hamburger

McDONALD'S, Hamburger
Scientific Name: NDB No: 21228
Nutrient Units per 100 grams

| | |
|---|---|
| Portion g | 105 |
| Water g | 45.67 |
| Energy kcal | 252 |
| Energy kj | 1053 |
| Protein g | 12.36 |
| Total lipid (fat) g | 9.29 |
| Ash g | 2.03 |
| Carbohydrate, by difference g | 30.69 |
| Fiber, total dietary g | 1.3 |
| Sugars, total g | 6.58 |
| Sucrose g | 0.27 |
| Glucose (dextrose) g | 2.28 |
| Fructose g | 2.93 |
| Lactose g | 0.15 |
| Maltose g | 0.95 |
| Galactose g | 0.0 0 |
| MINERALS | |
| Calcium, Ca mg | 121 |
| Iron, Fe mg | 2.64 |
| Magnesium, Mg mg | 2 0 |
| Phosphorus, P mg | 107 |
| Potassium, K mg | 203 |
| Sodium, Na mg | 507 |
| Zinc, Zn mg | 1.87 |
| Copper, Cu mg | 0.105 |
| Manganese, Mn mg | 0.257 |
| VITAMINS | |
| Vitamin C, total ascorbic acid mg | 0.6 |
| Thiamin mg | 0.247 |
| Riboflavin mg | 0.239 |
| Niacin mg | 4.544 |
| Folate, total mcg | 64 |
| Folate, food mcg | 64 |
| Vitamin B-12 mcg | 0.83 |
| Vitamin A, IU | 55 |
| LIPIDS | |
| Fatty acids, total saturated g | 2.938 |
| Fatty acids, total monounsaturated g | 3.170 |
| Fatty acids, total polyunsaturated g | 0.223 |
| Fatty acids, total trans g | 0.518 |
| Cholesterol mg | 27 |

The system can produce detailed food and eating logs for the user on request or at regular intervals. These logs can cover hours, days, weeks or longer periods and be presented verbally, visually or on a data file for computer analysis. The information contained in such a log can include eating times and duration, number and intensity of bites, chews or swallows, volume of liquids consumed, and if the food type is identified by the system or the user, in which case, the summary can also include, for example, caloric content and a breakdown of percentages of fats, proteins, sugars and carbohydrates. The system can also predict, for example, the current and cumulative glycemic index and cholesterol level of food eaten.

The messages described above can be pre-recorded by the user or a third party in a natural voice for later output by the system, or they may be output in a computer-generated voice.

The system can initiate a phone call or message delivery to the user's cellular phone, pager, or other portable communication system in real time with voice or text messages containing feedback relating to the amount of food eaten. Such an interruption in the eating behavior may be sufficient to condition people to eat less or otherwise modify their eating behavior.

The system can broadcast through a wired or wireless connection statistics, visual or audio messages that are displayed on a continually or periodic basis on a computer or television screen in real time. Such messages can occupy the entire screen or be displayed as a picture within a picture.

The system can provide summarized or real-time audio feedback for the user by transmitting information through a wired or wireless connection to an audio system of a vehicle.

The system can provide verbal feedback to the user unrelated to the functions listed above for the sole purpose of increasing the emotional connection of the user to the system or entertaining the user. For example, the system can greet the user by name with a good morning message, or wish the user goodnight with a message right before the system is turned off.

The user can download 'media content' which will interface between the sound analysis, behavior modification algorithms and the user. This personalized feedback can be customizable to have an 'attitude' relevant to the user, use humor and other rhetorical systems to convince the user to comply with the suggested behavior.

The system can periodically talk to the user with inspirational or encouraging messages intended to uplift or motivate the user.

The system can proactively recommend food types to the user before or during each meal by referring to a pre-selected nutritional plan. When dining outside, the user can provide the system with information relating to foods available at a restaurant and the system recommend to the user appropriate meals according to his or her needs. The system can also query the user as to whether the suggestions were followed. By so doing, the system can encourage healthy eating choices and keep track of the nutritional value of the user's food intake and provide information about trends and deviations.

Detailed description of the eating behavior embodiment of the system of the present invention is provided hereinbelow with respect to FIGS. 1-10.

Referring now to the Figures. FIGS. 1a-d illustrate several configurations of the system for monitoring and optionally modifying a behavior of a subject, which system is referred to hereinunder as system 10.

As is mentioned hereinabove, system 10 includes a sensor unit 12 and a processing unit 14. Sensor unit 12 and processing unit 14 can be integrated into a single device as is shown in FIG. 1c, or each component can be separately housed (FIGS. 1a-b), in which case, communications between sensor unit 12 and processing unit 14 is effected through a wired or a wireless (e.g. WiFi, Bluetooth, RF, infrared) connection (indicated by 16).

Sensor unit 12 can be mounted on or in a body region of the subject. Preferred mounting locations include behind or in the ear as shown in FIGS. 1a-c. Sensor unit 12 can be adhered to the surface of the skin, implanted subcutaneously, or implanted deeper in the body on or adjacent a bone or other suitable location. Of course, it will be understood that a variety of other locations are also possible, depending upon the nature of the behavior to be modified, the type and level of noise or other conditions to be detected, the nature of the sensor, user preference, and other factors.

Sensor unit 12 is designed capable of detecting and capturing activities (acoustic, physiological etc) of the subject. In order to perform such function, sensor unit 12 includes an acoustic sensor (preferably bone conduction, e.g. a Knowles Acoustics miniature microphone model number FG-3629-P16 or a Sonion Microtronic (www.SonionMicrotronic.com) 9721GX electret microphone modified by removing the filter that normally excludes low frequency acoustic energy covered with a 5 mm diameter hollow elastic bubble cover to couple acoustic energy from the skin to the microphone), and optionally additional sensors. In addition, sensor unit 12 also includes a power source (e.g. battery) and circuitry necessary for converting monitored activities to a signal which can be communicated to processing unit 14, as well as communication capabilities for enabling wired or wireless communication to and from processing unit 14.

Processing unit 14 includes a processor and software applications necessary for processing signals received from sensor unit as well as communication capabilities. The processor can be an embedded processor (typically found in digital hearing aids, wireless Bluetooth headsets, PDAs and cellphones, e.g., the ARM series), or a laptop, desktop or server processor (e.g., an Intel Pentium™ or Xenon™, an AMD Athalon™ or an IBM G5™). The processor can include a floating point unit, or not depending on the algorithms used.

Processing unit 14 can execute any operating system and software applications necessary from processing subject activities captured by sensor unit 12. Examples of software applications which can be used to process non-verbal acoustic energy signals are provided in Example 1 of the Example section which follows.

In a configuration of system 10 in which processing unit 14 is housed separately from sensor unit 12 (FIGS. 1a-b, d), processing unit 14 can be mounted on the subject (e.g. pocket of a shirt or pants, hand or on a belt, FIG. 1b), be accessed periodically by the subject (e.g., the laptop computer shown in FIG. 1a) or positioned remotely therefrom (e.g. the remote server shown in FIG. 1d). In the latter configuration, a docking station 18 can be utilized by the user to dock sensor unit 12 and communicate information between a remote server 20 and sensor unit 12 through a network 22 (e.g. computer network, cellular network, satellite network).

Processing unit 14 is selected according to the configuration of system 10. When housed with sensor 12 within a single device (FIG. 1c), processing unit 14 is typically a small embedded microprocessor. Such a fully contained unit is rechargeable, programmable and can communicate data by docking to an interface unit. When separately housed, processor unit 14 can be a laptop computer (FIG. 1a), a PDA, wrist watch or a cell phone (FIG. 1b) or a dedicated, body mountable system. In the remote configuration described above, processing unit is preferably a computer such as a personal computer (e.g., an IBM PC, or an Apple™ Macintosh™, workstation, a computer grid (parallel-computing cluster) and the like.

According to one preferred embodiment of the present invention, sensor unit 12 is configured for detecting and capturing acoustic energy through a bone conduction microphone. Such a sensor unit can be based on the "Inivsio" product (NextLink Inc. http://www.nextlink.to) which is a professional headset designed for use by special forces around the world.

The bone conduction microphone is designed to sense the acoustic energy generated within the mouth during eating. The microphone's analogue electrical output is transmitted to processing unit 14 for signal processing. A preprocessing stage filters out noise, normalizes the energy level, and segments the sampled sound into analysis frames. Features are then extracted from the signal using spectral signature analysis to identify waveforms with eating microstructure events (signatures). The extracted components are then evaluated by a statistical classifier that combines the observed data (the features) with prior information about the patterns to segment the input data into specific event categories such as chews, sips, and speech. The extracted acoustic energy patterns are then mapped into food intake events. Three preferred ways to measure food intake are by the type and number of bites and chews, and/or swallows and/or by the volume of the stomach. The volume of food per swallow is relatively constant, and averaged over the course of a day or a week, the caloric content of the total number of swallows is fairly constant as well. The Examples section which follows provides further description of such signal processing.

As is mentioned hereinabove, system 10 can also be configured for modifying a behavior of the subject. In order to enable such function, system 10 further includes a feedback element 24 which can provide the subject with feedback according to a behavior detected by system 10.

Feedback element 24 can be a speaker, a vibrating element, an electrode or any element capable of providing the subject with sensory information (auditory, tactile etc)

Audio feedback through the use of a speaker (in ear or bone conduction) is presently preferred. Such audio feedback can be used to:

Advise the user that a full portion has been consumed and to stop eating;

Suggest that the user have a snack instead of becoming overly hungry; and

Ask the user to name the type of food being consumed in cases where processing unit 14 cannot determine food type with high certainty.

The eating microstructure events will be mapped to food weight and caloric intake. Essentially, system 10 will deduce the food amount and type from the subject's eating microstructure patterns and additional user input if necessary, and then calculate caloric content accordingly.

Preferably, system 10 allows a user to be aware of their food volume input in real time and to stop eating whenever they have consumed the required amount of food. System 10 can alert the user to stop eating when sufficient volume was ingested (typically before completion of the meal), thereby reducing overall caloric input. Alternatively, the system can alert the user when not enough time has elapsed between meals or whether too much time has elapsed during a meal. Additionally, the system can coach the user to eat slower, and thereby eat less because the user's natural satiation mechanisms will be able to help them stop before over eating, or to take smaller bites.

The data collected by the system can be made available for analysis by, for example, the user, an external program, a consultant or a virtual community of users though the internet or other communication means. Data can be shared, analyzed and parameters of the system adjusted based on this process.

The shared system data could be used as part of a competition among the users to achieve certain goals. The user can receive expert analysis of the system data and regular coaching sessions with a health, nutrition or diet professional.

FIG. 2 illustrates in more detail the various hardware components of system 10 of the present invention.

System 10 includes a low power digital signal processor (DSP) 30 which processes a signal from sensor unit 12, extracts the spectral information, performs the analysis and generates the appropriate feedback when needed. The software and voice feedback files are stored in memory 32 (e.g. EERAM) on board. Both can be updated through one or more external communication ports 36. DSP 30 also performs power management and external communications. Preferably, all of these components are combined into one application specific integrated circuit (ASIC). A rechargeable or disposable battery 34 can power processing unit 14 and all its communication ports. System 10 can communicate via an optional externally powered modem, infrared link, or a USB port in order to retrieve software (update) and feedback modules. Processing unit 14 can also communicate with other systems such as a cell phone, cordless phone, PC via standard short range RF link such as WiFi or Bluetooth.

Sensor unit 12 (bone conduction microphone in this case) records the sounds made by chewing, swallowing, biting, sipping, and drinking. The salient acoustic features are extracted using a statistical-based pattern recognition system to classify the sounds into specific events. The output of the recognizer can be a hypothesized event sequence that can be used to track the flow of ingested food. The accuracy of the hypothesized output can be validated using a database of sounds annotated by a panel of human expert listeners.

Once an acoustic signal is generated by sensor unit 12 and communicated to processing unit 14, the signal is classified as outlined below.

A preprocessing module detects the presence of eating activity and automatically conditions the signal using automatic gain control on the analog signal prior to being digitized The amplitude of the electrical signal generated by sensor unit 12 is sensitive to the variations in the size of the ear canal as well as the eating style of the user. To compensate for these variations an analog preamplifier can be used to condition the signal. An automatic gain control system can be used to adjust the input gain guaranteeing a good use of the dynamic range while preventing clipping of the signal. The normalized signal is digitized using an analog-to-digital converter with a precision of 16 bits and a sampling rate of 8,000 Hz.

A signal processing module extracts a sequence of salient features from the digitized signal. The digitized signal can be parameterized using short-term analysis frames. The frame rate is $1/100$ ms and the analysis window is 500 ms. For each frame processing unit 14 can compute a log-filterbank energy vector with 20 components. The filterbank is designed to have higher resolution in the low frequencies than in the higher frequencies. This could be accomplished by using a bilinear transform. The warped filterbank is finally transformed into a cepstral vector with 12 components using a cosine transform. For each cepstral vector processing unit 14 can also compute the first- and second-order derivatives. The feature vector used for classification can be the combination of the cepstrum and its first- and second-order derivatives. Alternative methods of extracting features include log-filterbank energies and LPC Cepstrum methods. Features that capture the low frequency periodicity of the chew cycles can also be used to improve accuracy. Methods for extracting periodic information may be based on the autocorrelation method or the Fourier transform.

To classify the input signal into an optimal sequence of eating events processing unit 14 can search a state graph that represents all admissible state sequences. The Hidden-Markov models (HMMs) can be used to represent the microstructure of eating. A sample model is shown in FIG. 3. In this case, an eating even is represented as a bite followed by one or more chews and a swallow. The advantage of using HMMs is that the model parameters can be estimated without the need of having detailed time alignments for the underlying structure. This approach makes it possible to estimate model parameters for bites, chews, and swallows without detailed time alignment information which would be very tedious and difficult to obtain for large amounts of data. This approach only requires top level labels such as eating, drinking, and speaking. A panel of human expert listeners can annotate training data efficiently using a multimedia recording of the subjects that may include audio, video and position of the mouth or jaw. Once the HMM parameters are estimated it is possible to search for the most likely state sequence given the observed data. The optimal state sequence can be computed using a Viterbi search algorithm. The Viterbi search provides the optimal state sequence and time alignments information. The sequence of states is used to hypothesize the sequence of bites, chews, and swallows. Alternative methods of classifying the data include neural networks classifier. Another alternative is to detect chew events using a sliding window. For each window offset a score is computed using a Gaussian mixture model. Alternatively wavelet methods can be used to classify the relevant chew features. The Bayesian Information Criterion (BIC) (Schwartz, G., 1978. "Estimating the Dimension of a Model" The Annals of Statistics 6 (2), 461-464.) is an alternative method which can be used to segment the audio data. BIC can be used to detect changes in the audio data without using statistical models built for pre-determined acoustic classes.

Features such as chew count, chew, duration, and chew energy are computed as part of "eating" events. The features are fed to a mapping algorithm that estimates the weight of the ingested food based on a calibration of the known food weight reference available database used to train system 10. Alternative methods of estimating the ingested food weight include HMM's, neural network, and regression trees.

The statistical processing hardware and software techniques in the present invention are useful not only for characterizing the microstructure of eating events themselves, but also for processing higher level data patterns and signatures for the detection of ingested food weight or caloric content, detection of the beginning and ending time of meals, or even detection of where the user is relative to their overall diet plan.

FIG. 4, exemplifies software related functions of system 10 of the present invention.

The signals received from sensor unit 12 (and other input systems) are preferably first digitized. Preferably, digitization is optimized at twice the highest frequency sound that is to be recorded by applying automatic gain or log amplification to the signal of interest. Further, digitization is performed with bit depth sufficient to assure optimal signal discrimination for future processing. If necessary, the signal is normalized and ambient noise is subtracted from the signal. Spectral analysis or other data manipulation techniques are performed. Fast fourier transform (FFT) can be used with appropriate frequency ranges to obtain the power in each frequency band. Such processing can be restricted to signal segments of interest while using 'low resolution' spectral analysis to search for the beginning of an event and stand-by mode to conserve power between segments.

The spectral analysis and raw signal are utilized to extract features and categorize them with a time stamp and a fitness score. Other parameters might accompany each feature based on its nature. For example, a chew might have additional information such as intensity, frequency components (e.g. potato chips vs. meat) and duration. A swallow might have duration, liquid or solid bolus, etc.

Utilizing rules relating to the microstructure of eating, the software components can then determine if an event or events fit an acceptable pattern. The event log is edited as necessary to make sure it is consistent. The event log is updated with a beginning and ending entry for an episode. For example, bite, chew, swallow is one eating episode; sip, swallow is one drinking episode. Starting and ending a meal may create a meal episode.

Although system 10 can be used without need for calibration or training, preferably, a user might be asked to eat certain foods and drink liquids to train and calibrate processing unit 14. System 10 might ask the user to fill in a computerized form or interrogate the user verbally after each eating event or at the end of each day regarding what they ate during the first week or so to calibrate system 10.

System 10 might ask the user to categorize what they ate or drank by offering the most likely options based on historical or statistical precedence and wait for user input such as a click of their teeth or tongue. For example, if the user is drinking, system 10 might inquire if it's juice or alcoholic beverage. System 10 keeps track of user preferences and guesses based on historical patterns.

System 10 needs to detect, infer, or estimate the following based on historical data: swallow event, swallow volume, and energy density or what was swallowed. It is the cumulative product of the three that is of main interest to the user in real-time, at each feeding event, and as a daily summary.

By monitoring the event log as well as the current day of the week and time and looking at previously stored scenarios, system 10 can determine what scenario or eating context the user is in, for example, breakfast, lunch, snacking, sipping a mid afternoon hot coffee, weekend social dinner, home late night dinner, etc. Ambient noise might indicate whether the user is eating alone, with people, in front of the TV, etc. System 10 makes a best guess as an input to the goal analysis module as well as an update of user's custom scenarios' database. System 10 may ask the user to confirm or reject the system's guess as to the context of the eating event.

A user of system 10 which desires to diet using the system is preferably first asked to provide user specific information (e.g. fill out a computerized form). Based on this information as well as feedback from the user and other systems such as a digital scale, the user and system 10 create a set of goals regarding weight reduction or to maintain the desired weight over time. System 10 monitors user behavior and determines a strategy to achieve the goals. Based on the log of events and episodes, an algorithm determines the nature of the system's feedback to user. For example, if system 10 records fast eating, it might issue a message to slow down eating. If system 10 records too many cumulative swallows per meal, it may issue a warning to stop eating altogether. System 10 can interact with the user and ask the user questions in real time, such as to inquire about the user's eating and activity plans for the day, and only then determine the right course of action. For example, system 10 can detect overeating and ask the user if he or she intends to perform physical activity later that day. If so, system 10 increases the calorie budget for the meal, and then reminds the user later to work out.

For each feedback category and intensity, system 10 picks a speech snippet to communicate to the user. Snippets are recorded human voice (or computer generated human voice) that is stored or generated by category and intensity. Each such storage may contain many snippets and processing unit 14 will insure that a variety is used to maintain user interest and compliance. Examples include snippets of the user's own voice containing various promises the user makes to himself or herself, snippets of a voice of someone they know such as a coach, friend or family member, or snippets of a celebrity such as a TV personality whose feedback can be customized to the user's name. Additional output systems such as electrical stimulation, flavor transducers, etc. may be activated in addition to, or instead of, a speech snippet. User non-compliance will result in escalation of the feedback intensity or changes in the nature of the feedback based on a pre programmed template.

System 10 may elicit feedback from the user by speaking to him and asking for yes/no responses with a distinctive sound such as snapping of the fingers, clicking the teeth, or clicking the tongue on the roof of the mouth. The number of clicks may elicit different responses by the system. The user may prompt system 10 for information in a similar manner. System 10 may then report information such as level of compliance, goal attainment, etc. In this way, system 10 can be highly interactive and fun to use.

FIG. 5 illustrates various layers of system 10 and user interaction. Blocks 41 through 47 represent hardware options for parameters to measure. The detected parameters are represented by blocks 48 through 52. Blocks 55 through 61, 63 and 64 represent computed parameters or content provided by software. Blocks 62 and 65-70 represent the hardware layer and means of feeding back information to the user. Blocks 71-78 represent the applications and benefits to the user of using the system.

FIG. 6 depicts system 10 which includes a sensor unit 12 [incorporated into the minimal "Ear Unit" (EU) shown in FIG. 6] coupled wirelessly to a separate processing unit 14 [incorporated into the "Belt Unit" (BU) shown in FIG. 6] which can be within a few feet of the ear unit. Belt unit 84 can also be incorporated into another system such as a cell phone. Belt unit 84 comprises a pseudo-random number generator (PN Generator) 96 to spread the frequency spectrum over which ear unit 82 and belt unit 84 communicate, a voltage controlled oscillator (VCXO) 94, a digital signal processor (DSP) 86, a sequencer 100 that includes a set of logic gates to control the analog circuit elements, mixers 102 to mix incoming signals, band-pass filters (BPF) 104 and low-pass filter (LPF) 106 to allow signals of certain frequency through, a phase look loop circuit (PLL) 88 to synchronize the phase between two signals, an analog to digital converter (A/D) 112 to convert an analog signal to a digital number, and an antenna 108. Ear unit 82 has similar components to belt unit 84 with the addition of a tank circuit 98 consisting of at least one varactor diode, an amplitude clamp 116 which clips the signal to within set limits, a voice activated function (VOX) 114 which turns on the circuitry above a predetermined sound threshold, an oscillator (XO) 92 which generates a set frequency, and speaker 116.

In operation, belt unit 84 generates a signal in the desired band. This signal is received by ear unit 82 which modulates the phase and amplitude of the reflected wave. This can be accomplished by varying the resonant frequency of the tank circuit 98 using a varactor diode. If the tank circuit is resonant above the incoming signal frequency the load appears as an inductance and the reflected signal will be leading in phase. If the tank circuit is resonant below the incoming signal frequency the reflected signal will be lagging in phase. By using the chewing detector signal originating from sensor unit 12 to modulate the varactor, the resonant frequency is changed and the EU re-broadcasts a signal with the data information. To improve the interference immunity and sensitivity to other strong, coherent signals, the data is encoded with a pseudo-random (PR) digital string by a pseudo-random number generator 90. This PR string repeats after so many digits and the code is known to both ear unit 82 and belt unit 84. Since each set of ear unit 82 and belt unit 84 can have a different code, the interference between units can be greatly reduced. An additional feature is that each set of PR strings can be an independent analog signal. There can be multiple channels of data as well as a minimum and maximum level. This allows the system to know the absolute level of each sample, so even very slowly varying data can be sent.

Belt unit 84 receives this modulated signal and mixes it against the transmitted signal (without modulation) producing an intermediate frequency with the data. To make the system less sensitive to the close-in 1/f noise of oscillator 92 or voltage controlled oscillator 94, the pseudo-random number generator in ear unit 82 generates a discrete sideband in addition to the pseudo-random pattern. This allows the receiver to band pass filter the mixed down signal and amplify it to improve the dynamic range.

Since the received signal is the same signal as that being transmitted, the detection is always synchronous except for the time delay due to the propagation from the belt unit 84 to ear unit 82 and back. This time is very short—on the order of several nanoseconds, so the jitter and movement of the transmitter is cancelled out except for extremely fast movements. Thus, belt unit 84 source can hop around in frequency to further reduce interference problems without impacting the data. Signals from outside sources will not be synchronously detected and will average to zero.

The intermediate frequency is still modulated with a pseudo-random signal, so the next step for belt unit 84 is to lock onto the PR code and demodulate the audio information. This can be done with an early-late loop. The PR generator of Belt unit 84 will produce three strings of the code, each separated by a short time delay. By mixing each of these with the intermediate frequency signal, three values of correlation are generated. When the system is properly locked the early signal will be slightly de-correlated, the middle signal will be perfectly correlated, and the late signal will be slightly de-correlated. By looking at these three signals the local clock can be perfectly synchronized with the crystal oscillator in ear unit 82. Thus, the crystal oscillator of ear unit 82 becomes the master clock for the system.

Sync pulses are produced as a function of time, every predetermined number of sync pulses there would be a block for 'voice' data. This is a mechanism for transmitting voice data from belt unit 84 to ear unit 82. The sequencer on ear unit 82 counts the number of sync pulses and every N times it stops and 'listens' to see if there is data for it to present to the user. To do this, the transmitter's exact frequency needs to be known, so that ear unit 82 can tune to that frequency. Once tuned, ear unit 82 searches for a signal that has the PR code on it. If it identifies such a signal, it decodes it and enables the audio amplifier, and the user hears the message. During the audio receive time, ear unit 82 suspends the transmitting of data and is held in the receive mode until the PR sequence is no longer detected. At that point it goes back to transmitting its data.

During the audio receive mode, ear unit 82 is still using its internal crystal oscillator, but belt unit 84 is not correcting its local oscillator. Belt unit 84 is just holding the last value that it had for its oscillator correction. This being the case, the two oscillators will eventually drift far enough apart that the signal received at ear unit 82 will no longer be correlated. At that point, ear unit 82 will drop back into transmit mode and the audio will be muted. The time needed for the two clocks to drift out of sync is primarily related to the temperature change at either end, and the hold characteristics of the hold circuit. Since a voltage controlled oscillator is a natural integrator of phase, the two oscillators will always drift away from lock.

The link between ear unit 82 and belt unit 84 can operate, for example, at the 2.5 GHz ISM band. When the distance between ear unit 82 and belt unit 84 is one meter, the path loss is ~40 dB. Belt unit 84 will have reasonable antenna gain, assuming a dipole of about 3 dB, while antenna 108 of ear unit 82 will be much less efficient due to its smaller size. A reception antenna can be expected to have a gain of only about 5 dB for a short dielectrically loaded antenna. The conversion loss for modulating the reflection is assumed to be 10 dB, and belt unit 84 conversion loss and noise are assumed to be 10 dB as well.

Assuming 10 mW of transmit power, only thermal noise is added and no interferers, the expected signal to noise ratio would be about 63 dB which should be adequate to provide better than 10 bits of resolution for the data.

Because the exact orientations of ear unit 82 and belt unit 84 are not known and may change as a function of time, it may be desirable to include two sets of antennas on belt unit 84 to provide polarization diversity. DSP 86 of belt unit 84 can sample data from both antennas and choose the one with the better signal to noise ratio.

FIG. 7 depicts a system in which the communications between ear unit 82 and belt unit 84 is fully duplex, i.e. ear unit 82 transmits sounds or data to belt unit 84 and belt unit 84 transmits voice feedback or data to ear unit 82. An audio processor 118 conditions the audio signal for transmission using, for example a preamp and possibly a signal limiter and signal conditioner. The biggest difference between the above described configuration of system 10 and this configuration is in the use of the Phase Lock Loop (PLL) 88 as the source in ear unit 82. This has a large impact on the signal to noise ratio for the downlink data path. A link analysis shows that the signal-to-noise ratio increases dramatically. This allows the transmitted power at both ends to be reduced to 100 microwatts. The impact on belt unit 84 power is relatively small, but the impact on ear unit 82 power is larger. Therefore, this design will probably necessitate ear unit 82 to enter a sleep mode for much of the time. Since the units are pretty well synchronized, the overhead may not be too large. The overhead will be in locking up PLL 88 and perhaps re-syncing the PR generators, as well as some additional intelligence to control the wake-up sequence.

The systems described in FIGS. 6 and 7 can also be adapted so that ear unit 82 takes the form of a dental appliance and is placed in the mouth cavity as described elsewhere in this patent application. Using the design of FIGS. 6 and 7, no internal power source would be needed for the dental appliance, so the device could remain indefinitely in the mouth and mounted using techniques described elsewhere in this patent.

In addition to sensor unit 12 adapted for measuring the acoustic energy of food ingestion, system 10 of the present invention can also include sensor 110 for measuring caloric expenditure. Such measurements would enable more accurate system feedback.

Caloric expenditure is preferably calculated from measured metabolic rate. For example, system 10 can be configured capable of measuring metabolic rate through any one of several known approaches. System 10 can measure heart rate using one or more vibration sensors, plethysmographs, strain gages, EKG electrodes, accelerometers or microphones, either singly or in combination, in proximity to the carotid artery behind the ear region or at various regions of the external or internal ear and ear canal.

In order to measure heart rate, system 10 can interface with an implantable wireless EKG monitoring system comprising miniature EKG electrodes implanted under the skin and in wireless communication with a signal processing unit. Processing unit 14 can also wirelessly power the implantable electrodes which can be passive. The EKG system described here can also be implemented and used independently of the eating monitoring system, just like other remote EKG monitoring systems, with the added benefit of not having to affix wired or wireless electrodes on the skin surface.

An EKG sensor unit that can be utilized in system 10 of the present invention is illustrated in FIG. 8.

FIG. 8 illustrates an implanted telemetry capable unit 120 with outlying sensors 122 to sense several voltages around the heart from which the EKG waveform can be derived. Unit 120 can be roughly the size of a quarter and would be capable of measuring the voltages to sub-millivolt levels with a sampling rate to support more than 100 Hz of signal bandwidth. A minimum of three channels would be used. An integrated transmitter 124 would have a useful range of roughly a half of a meter or more.

A user-interface unit 130 which is similar in function to belt unit 84 described above can be utilized to communicate with unit 120. User-interface unit 130 would house an active transmitter 132 and be capable of receiving data from unit 120, and processing the data to derive useful information.

Unit 120 preferably employs a semi-passive transponder 126 embedded just under the skin over the heart. Transponder 126 would be small, and it would have several small wires which would run a few inches to sense voltages around the heart. These wires would also be used as the re-radiating antennae for transponder 126. The various (EKG) voltages would be amplified and then multiplexed on to the tuning line of a voltage controlled oscillator (VCO) 128. VCO 128, in turn, modulates a balanced-resonator tank circuit which is RF-connected to the wires. An incoming RF signal would be picked up by the wires and the phase at which it is re-radiated would be controlled by VCO 128 signal. By modulating VCO 128, rather than just base band modulating VCO 128, the problem of 1/f noise and low-frequency interference at the receiver is greatly reduced.

User-interface unit 130 transmits a fixed or variable frequency and the transmit signal is also used as the local oscillator for the receiver. The frequency can be moved as needed to avoid interfering signals. The transmitted signal is reflected as described above by the transponder, and after being mixed down against the transmitter signal, VCO 128 signal is recovered. From here, the FM voltage is extracted and the analog voltages de-multiplexed. Note that the receiver is completely synchronous: no interfering signals will have long-term averaging effects.

To allow synchronization and automatic calibration, the multiplexer in transponder 126 includes the minimum and maximum signal levels in the transmit sequence as shown in FIG. 9. The receiver can then easily scale the received voltages and eliminate drift and amplitude changes.

The bandwidth of this configuration is determined by several factors. Firstly, the sampling rate of the analog signals shapes the band pass, and a variable data rate can be employed to allow wider bandwidth signals if needed. Secondly, the receiver's FM detector can have an adjustable bandwidth. When the signal-to-noise (S/N) ratio is high, a wider bandwidth can be supported. This may be of interest if other sensors are included in the transponder.

The use of an FM tone on transponder 126 rather than directly modulating the reflection allows the receiver to have its gain spread over two frequency bands: the FM tone frequency, and the base band frequency. This is the same advantage that a heterodyne receiver has over a tuned-RF receiver. Additionally, the problem of 1/f noise of the diodes as well as the receiver are greatly reduced.

By using analog multiplexing the receiver can be the determiner of the bandwidth over a much wider range of frequencies. The receiver can decide how to deal with the analog data based on its S/N ratio. Under high-noise conditions, it may average, while under low-noise conditions it may extract more detail from the signal. It also simplifies the transponder by eliminating the need for an A/D converter.

By balancing the varactor-tuned resonator, the even-harmonic distortion is reduced resulting in less danger of interference from the transponder. Additionally, it provides a higher dynamic range and linearity.

One of the major problems of small electronics is that antenna gain is proportional to size. By having the probe wires do 'double duty' by serving both as electrical leads and the antennae, the antenna gain can be increased allowing for lower transmit power and better battery life.

While this wireless and passive EKG unit is one possible embodiment, other embodiments are possible as either stand alone EKG units or EKG units interfaced with other systems, such as a wristwatch, a cell phone or the eating monitor described here.

Furthermore, while this sensor system is illustrated for EKG electrodes, the design is generic and can be used for any sensor system where the sensor is part of a passive transponder that is energized and queried by a user-interface unit. The sensors associated with the transponder can measure temperature, pressure, humidity, strain, stress, forces, voltage, current or any other physical parameter of interest.

In addition to EKG measurements, system 10 can alternatively or additionally measure body motion, accelerations, blood pressure, body temperature, oxygen saturation, and/or breathing rate and depth through any of the traditional techniques known in the art to determine physical activity. For example, if system 10 is placed on or near the ear region, the pulse of the user can be heard or determined using a microphone or plethysmography on the earlobe, in the ear canal or tissue surrounding the ear. If the system is located in the mouth, it can determine the heart-rate using plethysmography using a sensor pressed against the mouth, tongue or cheek tissue. Alternatively, a system in the mouth can measure respiration rate and tidal volume, which is closely associated with heart rate, using a temperature sensor that detects the temperature difference of cool air inhaled into the mouth and warmer air being exhaled. Breathing sounds can also be recorded by the system and used to determine respiration rate and tidal volume.

The system can integrate the functions of or interface with a pedometer or GPS to measure distance walked or run by the user. The system can also interface through a wired or wireless connection with any other separate means for collecting physical activity data, such as a heart rate monitor on a watch or chest strap, odometer or pedometer.

System 10 can utilize any physical activity indicator alone or a combination of base metabolic rate, physical activity, gender, age, height, weight, medical records, medical background, and health status of the individual to calculate the caloric expenditure and full energy balance of the user. This information can be used by system 10 to formulate either independently or by interacting with the user, a physical training regiment for the user. Reminders to exercise and real time feedback regarding the training can be transmitted to the user through the audio interface described above. By way of example, system 10 can guide the user through a work out regimen using real time audio instructions into the user's ear. In addition, system 10 can use the acoustic energy signatures of the user's breathing or heartbeat to determine whether the user is complying with the workout plan. If, for example, the user is running, system 10 can hear the user's breathing patterns to determine workout intensity. If, for example, the user is lifting weights, system 10 can use the acoustic energy signature of the regular pattern of exhales between each exertion as a sign that the user is actually lifting a weight according to the training plan. Using these acoustic energy signature patterns, system 10 can provide the user with feedback such as counting the number of repetitions and training sets and provide training guidance and encouragement either in real time, before or after the workout.

System 10 can be utilized in conjunction with various diet plans. System 10 may be programmed to measure and analyze eating habits according to specific plans through varying levels of customization of the hardware, software or user interface. By way of example, system 10 can be configured to integrate into the Weight Watchers (WW) diet plan. System 10 can have an internal database of WW points for various foods and the user can query the database using verbal, tongue or teeth clicking or mechanical commands. System 10 can query the user regarding how many points they just consumed during or immediately after the system automatically or manually detects an eating event. It can also keep track of points banking.

Thus, the present invention provides a system which can be used to monitor and modify eating behavior of a subject.

Based on user reviews on the Epinion.com website, the key factors to success include the following:

(i) Emotional support at point of eating; such support can be provided by system 10 through rich audio feedback with emotional content in real time during eating events;

(ii) Portion Control; system 10 can provide real time food volume feedback;

(iii) User accountability; system 10 provides a tool to increase accountability (fewer excuses of mis-logged points, forgetting to log points, etc);

(iv) Internet subscriptions; system 10 can download data to a data storing and analysis program via a computer or a direct internet connection while the system is being recharged or via wireless link every time the user is near a computer;

(v) Meetings; the data generated in the systems and methods of the invention can be printed or downloaded to removable media or downloaded using a computerized system before or during a weight watchers (WW) meeting and the results analyzed together with the meeting staff;

(vi) Water; system 10 can keep track of the number of glasses of water the user drinks during the day to reach the recommended 8 glasses. The tracking can be done by listening to the swallowing sounds or registering the urination sounds throughout the day;

(vii) Weigh in; the user can manually update system 10 or alternatively system 10 can communicate with the weighing system in the "weigh ins" through a wired or wireless connection to update the user's weight in the system memory and recalculate the point budget automatically. System 10 is then re-programmed until the next meeting based on previous performance of the user and his or her upcoming goals; and (viii) Summary reports; system 10 can verbally or visually summarize for the user what they ate relative to what the WW plan recommends they eat at the end of each meal or end of each day. For example, the WW plan recommends 5 servings of fruits and vegetables. System 10 may be updated by the user as they eat each serving and the totals summarized for the user by the system.

Exercise; system 10 can keep track of activity levels as recommended by the WW plan.

The system of the present invention can also be configured to monitor and modify other behaviors.

For example, the system of the present invention can function as an interactive calendar and work productivity enhancer. This configuration of the present system can be used as an alarm clock with a verbal alarm message audible to the user. The system be integrated into or synchronize automatically or manually through a wired or wireless connection with a calendar software program and upload into the system memory upcoming appointments, including data fields for notes, agendas for meetings, verbal comments recorded by the user or third parties etc. The system can then remind the user of upcoming appointments, prepare the user for the appointment by reading aloud the agenda and prompt the user in real-time during the meeting with talking points. The system can help a person with a busy schedule stay on time by proactively alerting a person about an upcoming appointment.

The system can also be configured to receive and read emails or other text to the user while the user is engaged in other activities. The user can also record responses or original messages that can be sent as voice mail, a sound file attachment to an email, or text generated by a voice recognition system.

The system can further have situational awareness by analyzing ambient sounds and determining whether the user is typing on a keyboard, talking on the phone, talking with someone face to face, starting or ending a meeting, watching television or radio, playing of video games, or any other activity with a distinctive sound pattern. The specific activity can be further deduced by comparing the sound patterns to the user's activity schedule which is also stored on the system's calendar function. The system can also query the user for confirmation whether he or she is engaged in a specific task that the system believes it is hearing or that appears on the calendar at that time.

The system can summarize for the user a prioritized "to do list" at the beginning of each day and prompt the user to accomplish these tasks during the course of the day. At the end of the day, the system can manually or automatically prompt the user to confirm using voice, audible or mechanical input, whether each task was accomplished. The unfinished task can be carried over automatically to the next day by the system.

The system can be a useful tool for time management by providing summary statistics of how much time was spent doing each activity or meeting and comparing the person's actual completed tasks to a prioritized to do list.

The system can further act as a personal information manager by retrieving and storing personal information such as contact names, phone numbers, address, email addresses, etc through voice, audible or mechanical commands. The data for this function can be stored on an external phone/computer/PDA or on the system itself and synchronized with an external phone/computer/PDA.

The system can act as an audio interface for a virtual tour guide system in such places as tourist attractions, new cities or museums.

The system can listen to breathing, pulse rate, snoring and detect the user's motion and REM cycles during sleep and therefore be a useful therapy for sleep apnea, by for example partially awakening the user during apnea episodes with voice feedback or other mechanical or electrical stimulation. Partial awakening may restore natural breathing or change the user's sleeping position.

The system can play soothing messages or music to help the user fall asleep. In addition the system can transmit subliminal messages to the user during sleep.

The system can warn a user prone to heart attacks not to sleep too soon after eating a large meal, as this may increase the chance of a heart attack.

The system can also wake the user up during the appropriate stage of shallow sleep within a defined window of time. Awakening during shallow sleep, or non-rapid eye movement sleep, means a gentler awakening and allows the user to feel more refreshed and less groggy upon waking up. The system in this manner acts as an adaptive alarm clock or communicates with an external alarm clock or light source to gently wake the user up.

The system can further remind the user to take a drug or medication and then confirm that the user took the drug by registering the sound of the user swallowing water with the pill. The system can provide feedback regarding the ingestion of medications to the user and the health care provider in real time or in summary form. The system can remind diabetics to measure their blood sugar at regular intervals or before or after a meal.

The system can be used to teach languages by speaking to the user and listening to and correcting the user's use of the desired language. The system can also be used for a wide range of entertainment or lifestyle related activities. For example, the system can prompt the user in real time to prepare meals as an interactive audio cookbook, including timing the baking, cooking or food preparation process by reminding the user once the appropriate time has elapsed. The system can prompt a parent in the telling of a bedtime story to a child. The system can have one or more separate earpieces to enable additional people to hear audio from a common source. The system can broadcast ambient sounds, conversations or other noises to a remote listening system. The system can also be made fun to use with the verbal feedback being personalized, witty and even humorous. Celebrities or actors can be used as the voice in the system talking in a personalized voice to the user.

For purposes of security, the system can encrypt all incoming, outgoing and stored data making the system and its stored contents secure. The system may have embedded in it some form of biometric identification, such as chewing sound authenticator, fingerprint, retinal scanner, voice authentication or similar means for accessing the system, secure information or other external systems or facilities.

The system can also be configured to function as a "virtual coach" to encourage and instruct the user in physical conditioning. The system can utilize pre-programmed workouts and provide real time feedback of heart rate, breathing rate and depth, or caloric expenditure rate based on detecting these parameters, and to pace the user for an optimal workout using verbal, visual or other means described in this patent. In such an embodiment, the system can indicate to the user the target versus actual heart rate or exertion level, which may change over the course of a workout, thereby pacing the user. Additionally, since exercise carries the risk of dehydration or over-hydration, the system can estimate the exertion level of the user using techniques described elsewhere in this patent, the system can then instruct the user in real time to drink sufficient fluids and monitor the volume of liquids consumed by listening to the acoustic energy signatures of the drinking activity. The system, by querying the user, or by using integrated climatic sensors, or by being in communication with climatic sensors, may also take into consideration the climatic conditions such as temperature, humidity, sun exposure, and altitude in making the determination of how much the user should be drinking. The system can also be integrated with a perspiration sensor to determine perspiration rate which has a bearing on the requisite fluid and electrolyte intake. The system of the present invention can monitor fluid intake in order to comply with a medical plan. By way of example, people with kidney problems are encouraged by their doctors to maintain their fluid balance and ingest a certain volume of fluids per day. The system can provide a reminder to the user to drink the right volume of fluids or eat foods such as fruits that are high in fluids at the right time. The system, by monitoring the volume of fluid ingested using any of the techniques described in this patent, can compute and monitor the volume of actual ingested fluids and provide this feedback to the patient and the health care provider in real time or in summary form.

While not providing feedback to the user, the audio output portion of the system could be connected to an audio entertainment means, such as a separate CD or MP3 player, or alternatively the player could be an integral feature of the system. In a manner similar to the feedback the system provides regarding food intake, the system can report to the user on physical performance trends and statistics in a highly-interactive manner.

Voice detection and speaker units of the system can be interfaced with a communication system such as a cell phone or satellite based communication and/or tracking service. A third party can call the user and the user can talk immediately without the need to affix a headset or press a button. The third party can also monitor the noises in the environment of the system user. The third party can also program the system to notify the system user with certain messages at preset times or when certain events occur without the system user's required involvement. The system user can initiate a call or alarm to a third party through the voice commands of the user or by sound generated by the user that drives a selection of system actions without the need for the system user to press a button. Such a system can be useful for the handicapped, the elderly, children or animals.

The system can integrate a motion sensor and communication system. In the context of an elderly or disabled person living alone, the system can then detect extended periods of inactivity, a fall, or sleep irregularities and either call one or more preprogrammed numbers that will allow the user to talk to a third party whether it is a family member, health care professional, 911 or other monitoring service. Additionally, the system can automatically send a message to any of the parties listed above. Anyone calling the user would immediately be able to communicate with the user and hear the user's breathing, heart rate, voice and ambient noise or get data regarding and of the user's vital signs.

The system can also be used for underwater communications between divers or swimmers given that unlike normal speakers, bone conduction sound propagation is unaffected by the presence of water.

The system can also be configured capable of interacting with inanimate objects that contain embedded information, such as by way of example inventory items containing radio frequency identification (RFID) tags or other objects linked by wireless standards such as Zigbee. In this manner, the user can look at, point to, be in proximity with or touch an object and learn about it, such as for example through the audio transducers described in this patent.

The system can interface with a GPS, cell-phone or radio-based position tracking system, inertial navigation or other navigation systems and this information can be relayed visually or in audio form to the user. By determining the user's precise location, the present system can provide context dependent information and location based data and services. For example, if the system detects that the user walked into a specific restaurant, the system can use a database of what foods the restaurant offers and provide proactive feedback about the types of food to eat or not eat to best suit the diet plan of the user. The device would also know if the user is eating at home or away from home and tailor the feedback accordingly. The position information can also be relayed to a third party or an external system via a wired or wireless connection. Such a function may be useful for assisting the user to navigate on foot or in a vehicle while keeping their hands free. Such a system may further be useful for visually impaired individuals, for example. Such a tracking function can also be useful for keeping track of the location of individuals such as children, the elderly, the handicapped (by way of example, an Alzheimer's patients or physically handicapped individual) or animals. A third party is able to talk to the system wearer without the system wearer needing to perform any function to receive the call. The system, if connected to a position detector, can even automatically instruct the person to return home, for example.

In further embodiments, the system can be used for medical monitoring. For example, the system can be used to continually monitor the vital signs of the user and alert the user or a third party with any disorders discovered in a monitored parameter, such as by way of example only heart rate, heart rate variability, heart rate coherence, abnormal heart sounds, breathing, swallowing, blood pressure, galvanic skin response, excess perspiration, or fainting. The system can log cranial sounds for later playback to real time playback to a medical professional for diagnosing medical conditions through the cranial sounds. The system can monitor breathing patterns or brain waves and learn the patterns that occur prior to such disorders as fainting episodes, asthma or epilepsy attacks and warn the user proactively of an impending episode or attack.

The system may further be adapted for use in monitoring a person or animal. The system can act as a wirelesses communication system for infants to monitor their breathing or other vital signs. The system can also act as a wirelesses communication system for users in potentially dangerous situations such as soldiers, policemen, firefighters, astronauts, etc. Using a single analogue or digitally encoded transmission, a multiplexed data transmission, time division, frequency division or code division transmission technology, or multiple data channels, the system can relay separate channels of information, such as a user's voice, internal sounds such as breathing and heart rate, ambient sounds and the user's vital signs coded in an analogue or digital format, the user's location and motion to a third party or monitoring service. The source of the audio transmissions can be a single integrated microphone and sensing system monitoring one location on the user's body. Alternatively, the audio transmissions can be from several microphones or sensing systems in one or more locations of the user's body. The system can process the vital signals locally and only emit coded signals or alarms if and when certain thresholds are met. The system can also receive audio or digital data inputs from an external source and convert these to audible or visual commands or messages to the user.

The system can be used to sense the timing, duration and quality of a user brushing his or her teeth by recognizing and characterizing the distinctive sound pattern generated by such activity. This function can be integrated into a daily summary report regarding personal hygiene. The system can also proactively remind the user to brush their teeth after a meal in case the user has forgotten to do so.

Following bariatric surgery, the patient must strictly limit the amount of food they eat during the recovery period and while adjusting to their modified digestive system. The system can assist a person recovering from this form of surgery by counting the number of chews and swallows and providing real time feedback and a recovery plan for the patient. Alternatively, an embodiment of the system can be implanted in the patient concurrently with bariatric surgery of any sort and act as an alerting system in parallel to the effects of the surgery or an eating monitoring system to enable bariatric surgery patients to monitor and better manage their food intake post-operatively. Alternatively, the system can be implanted or mounted on the body surface within audible range of the stomach and trigger feedback based on listening to gastrointestinal or digestion sounds The system can also be used as noise cancellation headphones by monitoring the ambient noise arriving in the ear region of the user and then generating the opposite sound pattern and transmitting this cancellation wave through the bones of the user to the ear. This function is a bone-conduction noise canceling earphone that keeps the ear canal completely open and unobstructed. The system can also monitor ambient noises and sounds and warn the user when the level of such noise or sound is potentially dangerous and can cause damage to their hearing. Moreover, the system can serve as a hearing "booster" to supplement the natural hearing using bone conduction while keeping the ear canal completely open and unobstructed.

The system can also generate or play back white noise or relaxing sounds such as rain or the ocean waves to help people relax or concentrate without eliminating ambient sounds from the environment. This function could fade out after a preset time or fade in at a preset time to act as a sleeping aid or alarm clock, respectively. The system can help users meditate by providing the proper music and breathing instructions. The user's actual heart rate, heart rate coherence, breathing rates, and breathing depth can be measured and fed back to the user directly or used to trigger messages to the user by any of the means described in this patent application.

The system can further provide an adaptive alarm function. The system can be set to awaken the user after a preset time of sleep. For example, the user can program the system to wake him or her up after a 15 minute nap or at the end of 30 minutes, whichever comes first. The system would sense when the person falls asleep using breathing, motion, brain wave, or other forms of sleep sensing technologies and then awaken the user after 15 minutes. If no sleep state is registered, the system could nevertheless sound an alarm after 30 minutes as requested by the user. Similarly, the system can wake the person during shallow sleep within a preset window of time by measuring depth of sleep by incorporating or interfacing with sleep detection sensors known in the art.

The system can provide a voice recorder function. The system can periodically or continually record the user's speech and/or the conversations that the user participates in. This conversation log can later be accessed to listen to something that the user said or something that was said to the user. Retrieval of the conversation log can be through manual controls on the system, voice recognition software or the conversation log can be manually or automatically transferred to a computer or dedicated external storage system and accessed through software tools. Conversations can be manually or automatically transcribed into written reports and logged.

Such a function can be useful for recording reminders such as is done now with a Dictaphone or a small tape recorder, activity log, training, billing of time to various clients by professional service firms, memory aids, productivity log, archive, evidence collection, or personal coaching.

The system can be used to treat speech stuttering and other speech impediments. For example, the system can monitor the speech of the user and when the system detects stuttering or the user manually indicates that he or she is in a stuttering episode, the system provides an audio, mechanical, electrical or visual stimulus to assist the user in overcoming the stuttering.

The system can also be used as an accent coach. The system can pronounce pre-selected words with a specific accent that the user is trying to master. The system can detect when such words are pronounced incorrectly and in real time pronounce such words correctly. The loudness or tone of the message can be related to the user's need to correct pronunciation. By way of example, an almost correctly pronounced word would receive almost no correction or a correction in a soft positive tone while a mispronounced word would receive a loud correction or a correction in a harsher tone by the system. The system can have within it preprogrammed a limited number of words that are representative of the language and accent being learned. By mastering these words during the course of a normal conversation or in a learning session, the user can master the language or accent of choice.

The system can also be used for translation of languages. Using voice recognition or other means of data input, the user can request that the system translate a word, phrase or sentence into a language selected by the user. The system can then speak the translated phrase in the user's language and only the user would hear it. Using advanced voice recognition, the system can provide simultaneous real-time translation function to the user.

The system can also be used by actors, presenters, or public speakers as a text prompter. The system can have prerecorded on it or transmitted to it in real time prompts or the lines to be spoken by an actor or television presenter during a performance or broadcast and be unobtrusive so that only the actor or presenter knows that he or she is wearing the system.

The system can further be adapted to detect a decrease in a user's alertness by, for example, a position sensor detecting the dropping of the head, and the system can sound an alarm or provide other stimuli to awaken the user.

The system can act as a voice or sound activated remote control for external systems such as computers, garage doors, wheelchairs, entertainment systems, etc by interfacing with external systems through a radio, infrared, ultrasound or optical means.

The system can also measure the air temperature surrounding the user and be used to control, either manually or automatically, heating, ventilation or air conditioning unit (HVAC). This ensures that the temperature is properly set in the immediate area of the user.

The system can also be adapted to facilitate cessation of addictions and habits, including smoking. Smoking has a distinctive sound and effect on the breathing patterns of the smoker. The system can sense smoking events using, for example, smoking sound analysis or breathing rate analysis and provide feedback as per the descriptions above. The system may sense smoke or alcohol directly by incorporating a physical sensor of such items.

Further, the system can be adapted to help reduce alcohol consumption by sensing the alcohol level in the blood or in the breath and provide feedback as per the descriptions above.

The system can be adapted to reduce nail biting by sensing the closing of electrical loop between a hand and the mouth using electrical impedance sensors described above and provide feedback to make user aware of their activity.

The system may be adapted to monitor or modify the eating behavior of domesticated animals in much the same way as described here for human users. For example, an animal can be encouraged to eat by being provided with a mild electrical shock when it does not eat. Alternatively, an animal can be encouraged to stop eating when a predetermined amount of food has been consumed.

Further, the system can also be used to detect variances in an animal's eating or activity patterns so as to detect diseases at an early stage since disease is likely to affect the animal's eating behavior and physical activity pattern. Such deviations from normal patterns can be identified by the system and the appropriate person notified.

The system can be used to train animals in general by pre-recording commands and positive/negative feedback messages in the owner's or trainer's voice and sounding these messages or providing other means of mechanical or electrical feedback when the desired or undesired behavior is noted, either by the trainer or by the system itself.

The system can be an audio interface to external systems with voice commands or user-generated noises such as the click of the teeth or the click of the tongue. Illustrative examples include controlling an external computer, dialing and answering a telephone or cell phone, act as a combined microphone/speaker hands free system, interface with a navigation system with visual or audible navigation directions, to listen to music or other recorded audio content such as electronic books, or to listen to other radio transmissions such as is now used for security personnel. For example, the system could be used as an audio interface for an internet-enabled cell phone with the user transmitting commands to the phone using a clicking sound or voice commands and the phone supplying the user with the requested information, such as stock prices, weather, movie times or any other information available through internet-enabled phones.

Electrodes properly spaced on the user's head can be used to measure arousal (alpha waves), non-arousal (beta waves), day dreaming (theta waves) and deep sleep (delta waves). Information about the user's state can then be fed back to the user by any of the approaches described herein. For example, the system can audibly remind the user to focus on the task at hand if during the task the user's theta waves become active. Alternatively, a person who is trying to relax or think creatively can use audio biofeedback to increase his or her theta waves. The system can prompt the user on which thoughts or thought patterns can achieve the desired mental state. In general, the use of brain waves coupled with a continuous logging function and rich audio feedback gives the user means to become more relaxed, focused, creative or restful in their sleep.

The system can be integrated with or serve the function of a digital still or video camera. The user can record a voice tag along with each image or narrate a movie. For example, the camera can be integrated into the earpiece and be mounted in such a manner as to be collinear with the user's line of sight. By issuing a verbal, audible or mechanical command, the user can take a picture of the person or site that the user is looking at while simultaneously recording the person saying his or her name. The image with the voice snippet may be stored in the system memory and later recallable on the screen of the system or on an external computer. In this manner, a user can build a collection of visual and audible "business cards" and better remember people he or she meets throughout the day.

Face recognition software can be used to identify and recognize the individual in the photo. The user can then hear personal information about the individual through the audio transducer. The image taking function can also be triggered automatically by the act of shaking a person's hand, having the user say a phrase such as "Nice to meet you", bowing or by any other socially accepted way of greeting someone. In this manner, the person being greeted by the user of the system might not even be aware that their picture was being taken. The system may also store personal information about the user and either automatically or with the manual intervention of the user or a third party, the user's personal information may be transferred to an external system.

Personal information stored on the system such as interests or buying behavior can be made available by the system to third parties for the purposes of targeted advertisements that reach the user in an audio format.

The absolute or relative position of a limb or body part relative to the system can be detected using wired or wireless proximity sensors or accelerometers affixed to one or more limbs. This function can be useful for training athletes, dancers, rehabilitation, physical exercise and the like.

The system can be used in monitoring attention deficit disorder or attention deficit hyperactive disorder. The system can create a schedule of required tasks for the user and provide audio guidance during the day as to the tasks needing to be performed in a given timeframe. The system can then sense the amount of focus and concentration on the task at hand, using motion sensors for example, and provide feedback, encouragement and even log points towards a reward to encourage the desired behavior.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Monitoring and Analyzing Eating Microstructure Data

In a series of experiments, eating microstructure data was collected from 12 subjects eating a variety of foods within a controlled environment. The length of the recordings for 10 subjects was 20 minutes and for 2 of the subjects 10 minutes.

The subjects were asked to eat four crunchy foods (almonds, corn chips, Chex cereal, and apple), three soft foods (bagel, turkey, and banana), and two drinks (plain water, and carbonated soda). Each subject was asked to read two unique text paragraphs as part of the protocol. A sample protocol is as follows:

STEP ACTION DESCRIPTION
1 START
2 SAY Your age, your gender (male or female), your height, and your weight.

3 SAY I will eat a small bagel.
4 EAT A small bagel.
5 SAY I will drink a third of a cup of water.
6 DRINK A third of a cup of water.
7 SAY I will eat 10 almonds.
8 EAT 10 almonds.
9 SAY I will drink a third of a cup of soda.
10 DRINK A third of a cup of soda.
11 READ Text paragraph.
12 SAY I will eat 3 slices of turkey.
13 EAT 3 slices of turkey.
• . . . . . . . . .
29 STOP All of the subjects were asked to follow the same protocol, except for minor variations. Before the session, the in-ear bone conducting microphone, a Nextlink Invisio Standard modified to pass through sub-audible low frequency acoustic energy was mounted in the subject's right ear. The microphone was connected to a preamplifier that was connected to a personal computer. Initial test samples were recorded and the input gain of the preamplifier adjusted in order to cover the maximum dynamic range of the audio channel without clipping. Once the session started, all of a subject's data was put in a single audio file at a sampling rate of 16 KHz with 16 bits of precision. A sampling rate of 8 KHz. may be used with no significant loss in performance.

Recorded data was labeled using Adobe Audition 1.5 as shown for a representative sound sequence in FIG. 10. Waveforms were generally easily segmented using the following labels: Silence, Speech, Water, Soda, Bagel, Almonds, Turkey, Chips, Chex, Banana, and Apple. These labels were subsequently reduced to five symbols: "Speak", "Silence", "Drink", "Hard Chew", and "Soft Chew For each of the food segments, the number of chews was counted. Chews were counted by listening to a play back of the audio file. In some cases it was necessary to complement the audio with a visualization of the waveform plotted in the time and spectral domains. In the spectral domain, it is generally easy to visualize the energy pulses that correspond to the chews.

Additional monitoring of the eating microstructure can be obtained via other recordings including possibly, video recordings, an air microphone, or an accelerometer taped to the jaw. These additional data records will provide independent data sets for optimizing the detection of the microstructure events.

Software performance experiments were conducted using the Hidden Markov Modeling Toolkit (HTK) (Young, S. et. al., The HTK Book for Version 3.2, Cambridge University Engineering Department, Cambridge University), which is widely used for speech recognition research. Adobe Audition was used to record the sounds, listen to the sounds, analyze the spectrum, and label the data.

For the first set of experiments, the signal was parameterized using the Mel-Frequency Cepstral Coefficients (MFCC) (Furui, S. F. "Cepstral Analysis Technique for Automatic Speaker Verification IEEE Trans. Acoust., Speech, Signal Processing ASSP-29: 254-272). We chose MFCC as the starting point because it is a well understood technique in speech recognition research and provides several advantages. For example, by subtracting its time average, it is possible to compensate for variations in the transmission channel. The Mel warping is also useful for increasing resolution in the lower part of the spectrum. The first- and second-order difference of the cepstrum were used to parameterize the dynamic nature of the signal. It is possible to further optimize the feature set by developing techniques that provide maximum discrimination power.

The feature set can be further optimized based by using a larger eating sound database, such as one collected from a plurality of subjects.

For the models a 3-state left-to-right continuous-density hidden Markov model (Baum, L. E., T. Petri, et al. (1970). "A Maximization Technique Occurring in the Statistical Analysis of Probabilistic Functions of Markov Chains." Ann. Math. Statist. 41: 164-171) was selected. Each hidden Markov model corresponds to one of the 5 events being studied. By using a 3-state hidden Markov model, the left context, the middle of the event, and the right context could be modeled. Each state has a unique Gaussian mixture model with 8 to 16 components and no parameter tying across states (Huang, X. D., H. W. Hon, et al., "A Comparative Study of Discrete, Semicontinuous, and Continuous Hidden Markov Models." Computer Speech and Language 7(4): 359-368). The model was trained using approximately 120 minutes of recordings. The boot models were trained using time alignments for the classes. Because time alignments are only available for the eating segments, and not individual chews, each eating segment was partitioned uniformly into chew segments using the chew count information. The boot models were estimated using Viterbi alignments (Kruskal, J., Time Warps, String Edits, and Macromolecules: The Theory and Practice of Sequence Comparison. Reading, Mass., Addison-Wesley Publishing Co.). More accurate models were trained using several iterations of the Baum-Welch algorithm (Baum, L. E., T. Petri, et al. (1970). "A Maximization Technique Occuring in the Statistical Analysis of Probabilistic Functions of Markov Chains." Ann. Math. Statist. 41: 164-171).

In addition to the acoustic models, a stochastic language model (Jelinek, F., Statistical Methods for Speech Recognition. Cambridge, Mass., MIT Press) was also developed to constrain the search space using prior information available in the training set. Specifically a bigram language model was built using the five symbols in the search space. For example, the language model is expected to assign a high probability of transitioning from a Chew to a Chew whereas the probability of transitioning from a Chew to a Speak symbol is expected to be much lower. The optimal search is optimized empirically by adjusting the relative weight of the acoustic and language scores in the search.

After the signal is parameterized and acoustic and language models are trained, the remaining problem is to find the optimal state sequence given the observation sequence. The observation sequence is the sequence of MFCC parameters derived from the test set. To find the optimal state sequence efficiently we used a Viterbi search algorithm with a language model constraint. The output of the Viterbi search provides a hypothesized sequence of symbols including the start and end times.

To compute a measure of chew count accuracy, the following measures were implemented:

Chew Count Error (CCE). This is the average error in the test set without using time alignment information. The chews are counted in the reference and hypothesized symbol sequences as follows:

$$CCE = (ABS(<\#Chews> - \#Chews)/\#Chews) \times 100$$

Where "ABS" is the absolute value, $<\#Chews>$ are the number of chews provided by the eating monitor system being tested, and #Chews is the number of counts reported by the expert human listeners. Note that in the CCE if a Speak symbol is confused with a Chew, the Chew will be counted in <#Chews>.

A more restrictive measure is the Chew Miss Rate (CMR). In this case, only those chews were counted in segments that were reported as chews by the expert listeners. Note that, unlike CCE, if a Speak symbol is confused with a Chew, the Chew will not be counted in <#Chews>.

CMR=(ABS(<#Chews>−#Chews)/#Chews)×100(for chews hypothesized in chew segments only).

The False Alarm Rate (FAR) are segments that were incorrectly hypothesized as Chews in a non-Chew segment.

FAR=<#Chews>/#Chews(for Chews hypothesized in non-Chew segments only.)

Two systems were trained, the first one with 8 Gaussian density distributions per mixture and the second one with 16 Gaussian density distributions per mixture. Both systems modeled all 5 symbols. For each system one could search for the optimal language model weight. This is the relative weight between the acoustic and language scores used in the Viterbi search. The test set had 2 males and 2 female subjects and about an hour of recordings. Table 2 below presents the results after optimizing the language model weight. The model weight was optimized by changing its value in uniform increments and running the recognizer.

TABLE 2

Chew Recognition and Count Accuracy Results

| Gaussian Components | Number of Chews in Reference | Number of Chews estimated | CCE | Hits | CMR | False Alarms | FAR |
| --- | --- | --- | --- | --- | --- | --- | --- |
| 8 | 4378 | 5088 | 16.2% | 4857 | 10.9% | 231 | 5.3% |
| 16 | 4378 | 4299 | 1.8% | 4112 | 6.1% | 187 | 4.3% |

The expert human listeners counted 4,378 chews. Since the CCE, CMR, and FAR were significantly reduced after increasing the number of parameters from 8 Gaussians per mixture to 16, there may be sufficient data to train a greater number of parameters. Further improvements are anticipated as the amount of training data is increased along with the number of parameters in future experiments. In the second experimental analysis, the system hypothesized a total of 4,299 Chews with an error of 1.8% compared to the reference. The number of Chews accurately detected in the Chew segments was 4,112 which resulted in a CMR of 6.1%. The number of Chews incorrectly recognized in non-Chew segments was 187 resulting in a FAR of 4.3%.

One would anticipate dramatic improvement as the acoustic and language models are refined, the amount of data increased, and more discriminative features designed. Also, the sound recognition capability can be expanded to recognize a broader range of eating microstructure events in order to identify specific foods or types of food.

The acoustic vibrations captured by the bone conducting microphone are generated by multiple sources including jaw muscles, jaw bones, teeth, fluids in the mouth, compression of the food, breathing, vocal cords, etc. The signal is also affected by various factors including the size and shape of the subject, the eating style, e.g. chew force, chew rate, number of deglutitions per bite, duration of intra-meal pauses. Considering the signal variability, statistical pattern recognition techniques are used to model the eating microstructure and automatically classify the various acoustic events. Speech recognition research has shown that when classifying highly variable signals, statistical modeling consistently outperforms deterministic approaches (Huang, X. D., A. Acero, et al. (2001). Spoken Language Processing, Prentice Hall)

The main advantage of statistical methods is the ability to learn from the data resulting in much more adaptable and accurate systems when sufficient data is available. Moreover, the performance of a system trained on a large population of subjects could be dramatically improved using adaptation techniques. Adaptation techniques use a small sample of data from the test subject prior to recognition to adjust the system parameters. The current classification algorithms use Bayes' decision theory (Duda, R. O., P. E. Hart, et al. (2001). Pattern Classification Second Edition, John Wiley & Sons, Inc), which combines prior knowledge of the specified categories and posterior knowledge based on the observed data provided by the parameterized acoustic signal. Because the observation sequences will most likely be fully or partially labeled with the classified eating microstructure event categories, the EM algorithm (Dempster, A. P., N. M. Laird, et al. (1977). "Maximum-Likelihood from Incomplete Data via the EM Algorithm." Journal of Statistical Society ser. B 39: 1-38) is relied on to estimate model parameters. More specifically, Hidden-Markov models (HMMs) (Baum, L. E., T. Petri, et al. (1970). "A Maximization Technique Occuring in the Statistical Analysis of Probabilistic Functions of Markov Chains." Ann. Math. Statist. 41: 164-171) are used to represent the eating microstructure.

The advantage of using HMMs is that the model parameters can be estimated without detailed time alignment information (missing data), which is tedious, and sometimes impossible, to determine. The recognition system estimates model parameters for bites, chews, and swallows without using detailed time alignment information. Model training uses only top level labels such as eating, drinking, and speaking, plus the number of chews in every eating segment.

Once the HMM parameters are estimated, the next step is to search for the most likely state sequence given the observed data and the model. The optimal state sequence is efficiently computed using a Viterbi search algorithm (Kruskal, J. (1983). Time Warps, String Edits, and Macromolecules: The Theory and Practice of Sequence Comparison. Reading, Mass., Addison-Wesley Publishing Co). The Viterbi search will output the optimal state sequence and time alignment information which could be used to compute the recognition accuracy of the system. The state sequence will be used to hypothesize the sequence of bites, chews, and swallows. Refinements to this model include the use of a stochastic language model (Jelinek, F. (1998). Statistical Methods for Speech Recognition. Cambridge, Mass., MIT Press) to constrain transitions using prior knowledge obtained from the training set.

Accuracy of the present system can be improved by using supervised adaptation where the subject ingests food of known type and quantity for a short period of time. Statistical models are adapted once. Alternatively, the system can use unsupervised adaptation where the eating events are initially recognized using subject-independent models. The recognized events are used to adapt the models and generate more accurate recognition results.

Accuracy can also be improved by using time-of-day-dependent models. Models are adapted to time of the day to capture specific eating patterns in meals such as breakfast, lunch, and dinner. Different eating patterns would be predicted for weekdays versus weekends.

The present system can use stochastic grammars for improved event recognition. In another embodiment, the system can use confidence measures to improve chew count accuracy. A weighted chew count rather than a hard decision on the existence of a chew would be used to calculate an average of the log-posterior probability to compute a confidence measure of the number of chews. Trailing chews in a bite are expected to be weighted less than the leading chews.

The present system can perform a transformation of the acoustic signal to enhance intelligibility of chew sounds and facilitate count by the system.

As part of a low-power activity detection subsystem, a lightweight algorithm can be used to shutdown compute-intensive algorithms when there is a high probability that there is no food intake activity. The algorithm could key off of thresholds activity as well as make use of contextual information such as time of the day, day of the week, recent meal eating event information, historical data or behavior, and amount of food ingested.

The present system can choose among several behavior modification strategies and use Markov decision process to find the optimal strategy. Because food ingestion is constantly monitored, it is easy to determine if a specific strategy is successful or not.

In an alternative embodiment, the system can use wavelets to measure the chew count.

The algorithms can be developed using regression methods for predicting food mass ingested given chew feature information. Models can then be trained using multi-stream database. Streams include: (1) sounds of eating recorded using ear-microphone, (2) weight of food ingested measured using an electronic scale, and (3) video recording of subject's face to facilitate annotation.

A representative simple eating event sequence, of the sort capable of being identified with the current prototype software, would comprise a bite followed by one or more chews and a swallow, followed by more chews and a subsequent swallow or another bite to start the cycle over again, (as shown in FIG. 3).

To calculate the volume or mass of food in the stomach at any given time, one can utilize types of algorithms such as the following, presented by way of example only:

DEFINITIONS $V\text{in}(t)$ (in cc) is the detected volume entering the body. It is expected to have a form of a discrete delta functions.

$F\text{out}(t)$ (in cc/s) is the rate of food that leaves the stomach. It is assumed to be equal to a constant K, although more complicated expressions based on the actual accumulated volumes can also be considered. By way of example, a microphone, EMG muscle electrode, or other sensor can detect the acoustic energy or muscle activity associated with the passage of each bolus of ingested material through the pyloric sphincter, and assuming a constant volume of material per bolus, the device can therefore calculate the volume of ingested material leaving the stomach.

$V(t)$ (in cc) is the current volume in the stomach at time t.

Derivation:

First, assuming $V\text{in}(t)$ is 0 between t and $\Delta t$, and $V(t)$ is a nonzero value, after $\Delta t$ we have:

$$V(t+\Delta t)=V(t)-K^{*}t$$

But since $V(t)$ cannot be negative, we must have:

$$V(t+\Delta t)=\max(V(t)-K^{*}t, 0)$$

Now if at time $t+\Delta t$ the person received $V\text{in}(t+\Delta t)$ it simply adds to the value V:

$$V(t+\Delta t)=\max(V(t)-K^{*}t, 0)+V\text{in}(t+\Delta t)$$

Using the formula above, the current volume at any given time can be derived recursively based on its value at the previous discrete value of time.

In the above described experiments, it was noted that per individual, the total number of chews is highly correlated to the duration of an eating event such as the total time spent ingesting food during a meal. Therefore, in an alternative embodiment, instead of trying to detect individual chews, the system can simply measure the duration and timing of a discrete eating event such as a meal, or the accumulated time of eating throughout the day, and perhaps also the eating context, and from that deduce the number of chews and the weight of food ingested. The system could keep track of a user's individual eating times and encourage the user to eat for less time than the historical average time, thereby encouraging the loss of weight. In this scenario, there would be no need to detect and count individual chews. To improve accuracy, the system can be calibrated by the weight or volume of food ingested per chew or per unit of time per individual. In this embodiment, any of the detection means described in this patent need only to measure the duration of eating events by detecting when food is being ingested.

Example 2

Monitoring Energy Expenditure and Breathing Patterns

In a series of experiments, a Sonion Microtronic (www.SonionMicrotronic.com) 9721GX electret microphone 3.6 mm×3.6 mm×2.8 mm modified by removing the filter that normally excludes low frequency acoustic energy was covered with a 5 mm diameter hollow elastic bubble cover to couple acoustic energy from the skin to the microphone and mounted in an elastic support piece that positioned the microphone on the lower surface of the external ear canal just interior to the intertragic notch. The microphone and the support piece all fit within the confines of the outer rim of the conchal cavity of the human subject. A thin electrical wire transmitted the acoustic energy collected by the microphone to an analog to digital converter in a personal computer at a sampling rate of 16 KHz with 16 bits of precision and the resulting acoustic energy was captured and displayed using Adobe Audition 1.5. FIG. 11 shows the resulting trace of acoustic intensity versus time. Note that the user's heart rate is clearly discernable and matched perfectly with the signal generated by a Polar heart rate monitor (data not shown). From the heart rate and some additional information about the user, energy expenditure or exertion level can be calculated using techniques known in the art.

FIG. 12 shows a power spectrum of breathing sounds using the same microphone and data collection system used to generate the data in FIG. 11 where the human subject drew three breaths through the nose, three breaths through the mouth and snored three times. The trace of FIG. 12 depicts the energy levels at each of the measured frequencies as displayed on the Y axis as a function of time on the X axis. Each inhale and exhale event is clearly distinguishable by the regular drop in acoustic energy between events, correlating to the physiological pauses between each inhale and exhale. The type of breath can also be differentiated based on the distribution of energy in each event. For example, breathing through the mouth generates more mid tone energy and snoring generates more low frequency energy. Additionaly, exhales of breathing though the mouth tend to be louder than the inhales, while in snoring the inhale is generally louder than the exhale. Software applications utilizing, for example, the hidden Markov model described elsewhere in this patent, can be used to automatically find such features and distinguish between each separate breathing event, including the determination of the intensity and nature of the breath using the energy distribution at various frequencies, the rate of breathing, and the depth of breathing which is related to the duration of an inhale of exhale, and the ratio of the inhale to exhale intensities. Heart rate and breathing are highly correlated and either or both can be used in estimating exertion or energy expenditure. The use of breathing patterns can be used as the basis for an activity monitor as well as stress relaxation techniques and other applications described in this patent.

Example 3

Detection of Chewing Activity Using Accelerometer and Microphone Sensors

A Knowles BU-3173 miniature accelerometer and the Sonion Microtronic 9721GX electret microphone used in Example 2 were placed in contact with the skin of the skull a few millimeters above the highest point of the connection of the helix of the ear to the skull (this is close to the area where the horizontal temple piece of eye glasses rest on the ear). A plastic bracket that wrapped around the back of the ear similar to a behind-the-ear hearing aid held each sensor in contact with the skin. The muscle group immediately under the skin in this area is called the temporoparietal muscle. The accelerometer was mounted on the left side of the head and the microphone on the right side. The electrical signals generated by the sensors were fed through thin wires into a digital oscilloscope as the subject chewed gum eight times. The subject was silent and did not move before and after the eight chews. FIG. 13 shows the oscilloscope traces as a function of time. The blue trace is the signal from the accelerometer measured on the left scale in millivolts and the red trace is the signal from the microphone measured on the right scale in millivolts. Eight signals peaks are clearly visible in the blue accelerometer trace corresponding to the eight chews. Eight double peaks and dips are clearly visible in the red microphone trace corresponding to the eight chews. Therefore, detection of chewing activity by sensing either motion of the skin or sound propagated from within the head is feasible.

Example 4

Detection Motion Using a Microphone Sensors

A subject was fitted with the Sonion Microtronic 9721GX electret microphone, mounting bracket, and experimental set up used in Example 3. The subject started to jog and the acoustic energy from the jogging motion was transferred through the skull to the microphone. The trace in FIG. 14 shows the voltage of the microphone as a function of time (in seconds). Fifteen peaks and dips are clearly discernable in the trace corresponding to the fifteen steps of the user's jogging. Therefore, the use of acoustic energy to measure physical activity is demonstrated.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A system for monitoring ingestion activity of a subject comprising:
    (a) a sensor mountable on or in a body region of the subject, said sensor being configured for mechanically sensing jaw motion by sensing tissue deformation in an ear resulting from said jaw motion; and
    (b) a processing unit being capable of processing said jaw motion and deriving an ingestion activity related signature therefrom, thereby monitoring the ingestion activity of the subject.

2. The system of claim 1, wherein said jaw motion is caused by biting or chewing.

3. The system of claim 1, wherein said sensor is a strain gauge.

4. The system of claim 1, wherein said sensor is mountable on a head of the subject.

5. The system of claim 1, wherein said sensor is mountable within an ear canal of the subject.

6. The system of claim 1, wherein said sensor and said processing unit are housed in a single device.

7. The system of claim 1, further comprising at least one additional sensor selected from the group consisting of a heart rate sensor, an accelerometer, a skin conductance sensor, a muscle tone sensor, a blood sugar level sense, a bite sensor and a stomach contraction sensor.

8. The system of claim 1, further comprising at least one feedback device.

9. The system of claim 1, wherein said sensor is an accelerometer.

10. The system of claim 1, wherein said sensor is a bone conduction microphone.

11. The system of claim 1, wherein said sensor and said processing unit are housed separately.

12. The system of claim 11, wherein the sensor is adapted to communicate with the processing unit.

13. The system of claim 12, wherein the sensor is adapted to communicate with the processing unit wirelessly.

14. The system of claim 12, wherein the sensor is adapted to communicate with the processing unit via a wired connection.

15. A method of monitoring ingestion activity of a subject comprising:
   (a) mechanically sensing jaw movement by sensing tissue deformation in an ear resulting from said jaw motion; and
   (b) processing said jaw movement and deriving an ingestion activity related signature therefrom, thereby monitoring the ingestion activity of the subject.

16. The method of claim 15 further comprising mounting a jaw motion sensor on the subject's head.

17. The method of claim 15 further comprising mounting a jaw motion sensor within an ear canal of the subject.

18. The method of claim 15 wherein the processing is performed at least partially in a processing unit, the method further comprising communicating jaw motion information from the sensor to the processing unit.

19. The method of claim 15 further comprising sensing at least one additional patient parameter selected from the group consisting of heart rate, skin conductance, muscle tone, blood sugar and stomach contraction.

20. The method of claim 15 further comprising providing feedback to the subject based on the sensed and processed jaw motion.

21. A device for monitoring food and/or drink consumption of a subject comprising:
   (a) a sensor configured for sensing ingestion activity of the subject from tissue deformation in an ear of the subject; and
   (b) at least one feedback device for providing feedback relating to said ingestion activity of the subject, wherein said feedback device is capable of modifying a type of feedback according to a change in said ingestion activity of the subject.

22. The device of claim 21, further comprising a microphone for receiving acoustic input from the subject.

* * * * *